United States Patent
Hausmann

(10) Patent No.: US 12,370,566 B2
(45) Date of Patent: Jul. 29, 2025

(54) METHOD FOR ASSEMBLING DISPENSING DEVICES, AND DISPENSING DEVICE

(71) Applicant: BOEHRINGER INGELHEIM MICROPARTS GMBH, Ingelheim am Rhein (DE)

(72) Inventor: Matthias Hausmann, Ingelheim am Rhein (DE)

(73) Assignee: BOEHRINGER INGELHEIM MICROPARTS GMBH, Ingelheim am Rhein (DE)

( * ) Notice: Subject to any disclaimer, the term of this patent is extended or adjusted under 35 U.S.C. 154(b) by 220 days.

(21) Appl. No.: 17/802,836

(22) PCT Filed: Mar. 15, 2021

(86) PCT No.: PCT/EP2021/056511
§ 371 (c)(1),
(2) Date: Aug. 26, 2022

(87) PCT Pub. No.: WO2021/185751
PCT Pub. Date: Sep. 23, 2021

(65) Prior Publication Data
US 2023/0103823 A1 Apr. 6, 2023

(30) Foreign Application Priority Data
Mar. 18, 2020 (EP) ..................................... 20163813

(51) Int. Cl.
*B05B 11/10* (2023.01)
*A61M 15/00* (2006.01)

(52) U.S. Cl.
CPC ..... *B05B 11/1047* (2023.01); *A61M 15/0065* (2013.01); *A61M 2207/10* (2013.01)

(58) Field of Classification Search
CPC ............... B05B 11/1047; B05B 11/105; B05B 11/1091; A61M 15/0065; A61M 2207/10;
(Continued)

(56) References Cited

U.S. PATENT DOCUMENTS

| 7,284,474 B2 | 10/2007 | Eigemann |
| 7,950,388 B2 * | 5/2011 | Kunze ................. B05B 11/0054 128/200.22 |

(Continued)

FOREIGN PATENT DOCUMENTS

| EP | 1426662 A1 * | 6/2004 | ............ A61M 37/00 |
| EP | 2275160 A1 * | 1/2011 | ............ A61M 11/02 |

(Continued)

OTHER PUBLICATIONS

International Search Report for corresponding PCT Application No. PCT/EP2021/056511, 4 pages, dated Jun. 1, 2021.
(Continued)

*Primary Examiner* — Bob Zadeh
(74) *Attorney, Agent, or Firm* — Calderon Safran & Wight P.C.; David S. Safran

(57) ABSTRACT

Methods and apparatus for assembling dispensing devices and/or for dispensing a medicament include a sealing element fixed in a receiving space of the dispensing device with a specific assembly parameter. A plurality of sealing elements is produced in batches, and all sealing elements of a batch are fixed with the same assembly parameter.

19 Claims, 8 Drawing Sheets

(58) Field of Classification Search
CPC .. A61M 2202/0468; A61M 2205/0216; A61M 2207/00; A61M 11/007
See application file for complete search history.

(56) References Cited

U.S. PATENT DOCUMENTS

| | | | | |
|---|---|---|---|---|
| 8,061,350 | B2* | 11/2011 | Boeck | F04B 53/16 |
| | | | | 128/200.22 |
| 2004/0134495 | A1 | 7/2004 | Eigemann | |
| 2007/0282276 | A1 | 12/2007 | Boeck | |
| 2012/0325204 | A1* | 12/2012 | Holakovsky | B05B 11/0054 |
| | | | | 128/200.23 |
| 2014/0145436 | A1* | 5/2014 | Charcenko | F16L 5/06 |
| | | | | 285/355 |
| 2017/0209344 | A1* | 7/2017 | Babbs | A61J 15/0053 |
| 2023/0103823 | A1* | 4/2023 | Hausmann | B05B 11/1047 |
| | | | | 222/401 |

FOREIGN PATENT DOCUMENTS

| | | | | |
|---|---|---|---|---|
| FR | 3085734 | A1 * | 3/2020 | ........... B05B 11/105 |
| GB | 2467904 | A * | 8/2010 | ................ A61J 1/06 |
| JP | 2004527087 | A * | 9/2004 | |
| JP | 5054017 | B2 * | 10/2012 | ........ A61M 15/0065 |
| WO | 9606011 | A2 | 2/1996 | |
| WO | 2000049988 | A2 | 8/2000 | |
| WO | 2004053362 | A1 | 6/2004 | |
| WO | 2007051536 | A1 | 5/2007 | |

OTHER PUBLICATIONS

International Preliminary Report on Patentability and Written Opinion for corresponding PCT Application No. PCT/EP2021/056511, 6 pages, dated Sep. 20, 2022.

\* cited by examiner

METHOD FOR ASSEMBLING DISPENSING DEVICES, AND DISPENSING DEVICE

BACKGROUND

The present invention relates to a method for assembling dispensing devices for dispensing a medicament and to a dispensing device for dispensing a medicament.

In particular, the present invention relates to the arrangement or assembly of a sealing element in a receiving space of the dispensing device that is assigned to the sealing element. The sealing element is preferably used to seal a conveying element used for conveying a medicament out of a container of the dispensing device. For this purpose, the sealing element in the fully assembled dispensing device is in sealing contact with the conveying element. The conveying element is preferably movable relative to the sealing element. In particular, the conveying element is moved relative to the sealing element to convey the medicament.

When sealing the conveying element by means of the sealing element, various requirements have to be met. On the one hand, a reliable seal should be ensured, even if the dispensing device is stored for a long time, or has a long service life. In other words, a permanent and reliable "static seal" of the conveying element should be achieved by the sealing element. On the other hand, a reliable seal should be ensured when the dispensing device is used, in particular when the conveying element moves relative to the sealing element. That is, a so-called "dynamic seal" should be achieved.

The desired sealing, both in the static case in which the sealing element is at rest relative to the conveying element, and in the dynamic case in which the conveying element is moved relative to the sealing element, may pose different, mutually contradictory requirements. A particularly good static seal can be achieved in that the sealing element rests against the conveying element over as large an area as possible and/or as firmly as possible. However, this is disadvantageous for the dynamic seal, since a firm contact of the sealing element over a large area of the conveying element can lead to increased abrasion or damage to the sealing element, and to an increased expenditure of force when the conveying element is moved relative to the sealing element, or to a slower movement of the conveying element.

Furthermore, for a good static seal, the sealing of the conveying element by the sealing element should be as diffusion-tight as possible. Diffusion through the sealing element should therefore be prevented or at least minimized.

WO 2004/053362 A1 relates to a piston pump system having a piston which is guided in a guide tube and which can perform a lifting movement along its longitudinal axis, with an O-ring seal held in a groove being provided in the guide tube and sealing the piston. It has been recognized that a good seal can be achieved if the degree of filling of the seal in the groove is optimally adjusted. The "degree of filling" corresponds to the ratio of the volume of the (undeformed) seal to the volume of the groove. It is proposed to use a degree of filling of more than 90%—that is, to use a sufficiently voluminous sealing ring.

A method by which reliable sealing of a conveying element of a dispensing device is to be achieved is known, for example, from WO 2007/051536 A1 or US 2007/0282276 A1. It has been recognized that the sealing elements are subject to certain manufacturing tolerances, as a result of which the sealing elements of different batches differ in size, such that reliable sealing is problematic. To eliminate this problem, a size of the sealing elements that corresponds in particular to the volume is determined for each batch of sealing elements. Each batch of sealing elements is assigned to a specific group of components of the dispensing device, the components each forming a groove-shaped receiving space for the sealing element, and the different groups of components differing in the size of the receiving space. Each batch of sealing elements is then combined with a specific group of components of the dispensing device so that a desired degree of filling and thereby a good seal by the sealing element are achieved.

In the aforementioned method, there is an increased storage requirement for storing the different batches of sealing elements and the different groups of components. In addition, the method cannot be used flexibly for different sealing materials.

SUMMARY

It is an object of the present invention to provide a simple and flexible solution for reliably and permanently sealing a conveying element of a dispensing device for dispensing a medicament.

According to the proposal, a sealing element is installed in a dispensing chamber of a dispensing device with a previously determined assembly parameter.

The assembly parameter can be determined individually for each sealing element, or randomly for a batch of sealing elements.

The assembly parameter can be determined either in a receiving space of the dispensing device or, in particular in the case of a random determination, in a test system. For this purpose, the test system preferably has a receiving space which, in particular, has the same dimensions as the receiving space of the dispensing device.

In particular, the present invention relates to a method for assembling dispensing devices for dispensing a medicament, and to a dispensing device for dispensing a medicament, wherein a sealing element with the specific assembly parameter is arranged and fixed in the receiving space of the dispensing device.

The sealing element arranged in the receiving space of a dispensing device or test system is preferably deformed, and the assembly parameter is determined in the process on the basis of the deformation behavior and/or friction behavior of the sealing element during the deformation.

After the assembly parameter has been determined, the sealing element, or a further sealing element to be installed, is fixed in the receiving space of a dispensing device utilizing the assembly parameter.

The dispensing device that is assembled or in which the sealing element is fixed can be the same dispensing device in which or in whose receiving space the sealing element was arranged to determine the assembly parameter. However, it is also possible that the dispensing device that is assembled or in which the sealing element is fixed is a different dispensing device or a different copy of the same dispensing device or has a different copy of the same receiving space than the dispensing device or receiving space that was used in the determination of the assembly parameter. This is the case in particular with the batch method explained in more detail below.

By determining the assembly parameter based on the deformation behavior and/or friction behavior, and/or by using the assembly parameter, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

The assembly parameter is preferably an adjustable, in particular geometric, value that must be observed when the dispensing device is assembled and/or which is implemented in the completely assembled dispensing device. The assembly parameter can preferably be variably prespecified in the configurations of an assembly process. The assembly parameter is preferably a geometric parameter—in particular a preferably-relative position of a component or a dimension—such as a height of the receiving space of the dispensing device, for example. In particular, the assembly parameter is a position of a fixing element relative to a guide element, the sealing element being fixed in the guide element or in a receiving space of the guide element by means of the fixing element.

A plurality of sealing elements is preferably provided in batches. An assembly parameter is preferably determined separately for each batch using a random sample of sealing elements of this batch. This assembly parameter which is determined for the batch is preferably used each time a sealing element of the batch is fixed in a receiving space.

The assembly parameter for a batch is preferably determined separately or independently, in particular separately with respect to time and/or space, from the assembly of sealing elements or dispensing devices, preferably in a different system from the assembly of sealing elements or dispensing devices. In other words, the determination of the assembly parameter and the assembly of dispensing devices are preferably carried out separately from one another. This method is also referred to below in particular as the "batch method."

The assembly parameter is preferably selected in each case in such a way that the same deformation value of the sealing element in the receiving space results for the completely assembled dispensing devices for different batches, or independently of the batch. The deformation value is in particular a measure of how much the sealing element is deformed—in particular, compressed. As a result, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

During assembly, the deformation value is preferably adjusted by means of a position, in particular an axial position, of a fixing element and/or contact element with which the sealing element is deformed. In particular, a specific deformation value of the sealing element is thus implemented by means of the assembly parameter.

To determine the assembly parameter of a batch, an assembly parameter is preferably first determined separately for each sealing element in the random sample, and a mean value of these assembly parameters determined separately or for individual sealing elements is defined as the assembly parameter for all sealing elements of the batch. In other words, the assembly parameter determined for a batch is preferably a mean value from a plurality of assembly parameters. As a result, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

During the determination of the assembly parameter, a central element is preferably passed through an opening of the sealing element, and the volume of the receiving space is reduced or limited by the central element. This is conducive to easier assembly and consistent quality in the manufacture or assembly of a plurality of dispensing devices, in particular in an automated process.

The central element is preferably removed from the receiving space and/or the opening of the sealing element after the sealing element has been fixed in place. The use of the central element offers the advantage that the deformation of the sealing element during the determination of the assembly parameter corresponds to a deformation that the sealing element has when the dispensing device is completely assembled, without the conveying element having to be assembled when the assembly parameter is determined. The use of the central element is therefore conducive to a simple and reliable determination of the assembly parameter and/or to ensuring a reliable seal and/or sealing effect. Furthermore, the use of the central element makes it possible to determine the assembly parameter independently of the assembly of the sealing element or before the assembly of the sealing element and/or in a different system than the assembly of the sealing element. This is conducive to an optimal process during the determination of the assembly parameter and/or the assembly of the sealing element, in particular in an automated process.

It is preferred that a diameter of the central element corresponds to a diameter of a conveying element of the dispensing device, which conveying element is designed to convey medicaments, in particular out of a container of the dispensing device, and/or which is assigned to or connected to a discharge device of the dispensing device for generating an aerosol. This is conducive to a reliable seal and/or sealing effect.

The number of sealing elements in the random sample is preferably less than 50‰, preferably less than 20‰, in particular less than 10‰, particularly preferably less than 5‰, very particularly preferably less than 2‰ of the number of sealing elements of the batch. This allows for minimal difficulty in the determination of the assembly parameter, and/or a quick and efficient determination of the assembly parameter.

Alternatively or additionally, the volumes of the sealing elements of a batch preferably deviate by less than 10%, in particular less than 5%, particularly preferably less than 4%, from the target volume or mean volume of the sealing elements of the batch. This is conducive to consistent quality in the manufacture or assembly of a plurality of dispensing devices, in particular in an automated process.

The features explained above relate in particular to a method also referred to below as the "batch method," in which the sealing elements are produced or are available in batches and an assembly parameter is initially determined for each batch on the basis of a random sample, wherein this assembly parameter is later used for the installation of each sealing element of the batch.

However, it is also possible to first determine the assembly parameter for a sealing element each time a sealing element is installed, and then, in particular immediately after determining the assembly parameter, to fix the sealing element in the receiving space using the determined assembly parameter. In particular, this is independent of whether the sealing elements are provided in batches and/or have been produced in batches and/or whether the individual sealing elements differ greatly from one another or not. The method explained below, which is also referred to as the "individual method" in the further description, is therefore particularly advantageous if individual sealing elements differ greatly from one another—but can also be implemented for any sealing elements, in particular those that are very similar within a batch.

In the individual method, in which the sealing element arranged in the receiving space is preferably also deformed and an assembly parameter is determined during the deformation, as described above, the sealing element is immediately fixed in the receiving space after the sealing element has been deformed and the assembly parameter has been determined by means of a fixing element and/or contact element acting on the sealing element. As a result, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

In the individual method, in which the sealing element is fixed in the receiving space immediately after the sealing element has been deformed and the assembly parameter has been determined, the assembly parameter is preferably determined separately for each sealing element to be installed and is used in each case only when fixing the sealing element for which it was determined. This is advantageous to ensure a reliable seal and/or sealing effect in the case of sealing elements that differ greatly from one another.

The aspects explained in more detail below preferably apply both to the method, in which the assembly parameter for all sealing elements of a batch is first determined using a random sample and the assembly (using the assembly parameter) is carried out separately from the determination of the assembly parameter (batch method), as well as to the method, in which an assembly parameter is determined separately for each sealing element and the sealing element is fixed in the receiving space immediately after the determination of the assembly parameter using this assembly parameter (individual method).

It is preferred that the assembly parameter represents a position, in particular an axial position, of a fixing element and/or contact element relative to a guide element of a dispensing device, or corresponds thereto, or that the (relative) position of the fixing element and/or contact element is defined or specified by the assembly parameter. In this case, the guide element preferably at least partially comprises or forms the receiving space. Furthermore, the receiving space is preferably delimited by the fixing element and/or contact element.

The fixing element and/or contact element is preferably designed for fixing the sealing element in the receiving space, and/or the fixing and/or contact element fixes the sealing element in the receiving space. The contact element is particularly preferably arranged or can be arranged between the sealing element and the fixing element, the contact element directly contacting the sealing element and fixing it in the receiving space. The contact element is preferably fixed or can be fixed by means of the fixing element. In particular, the contact element is thus directly fixed by means of the fixing element, and the sealing element is thus indirectly fixed in the receiving space. Alternatively, the contact element can also be designed as a single piece together with the fixing element. As a result, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

Different assembly parameters preferably correspond to different volumes of the receiving space or to variable differences between the volumes of the sealing element and the receiving space. The volume of the receiving space can therefore be adjusted or varied by the assembly parameter, such that manufacturing tolerances and differences in size and/or material of sealing elements and/or the receiving space can be compensated for. This is conducive to a reliable seal and/or sealing effect and consistent quality in the production of a plurality of dispensing devices, in particular in an automated process.

The assembly parameter is preferably selected or determined in such a way that, when the sealing element is fixed, a deformation value corresponding to the deformation of the sealing element reaches or exceeds a threshold value. Different threshold values are preferably provided for different sealing elements that differ, for example, in their outer shape and/or in the material from which they are made. The threshold value is preferably prespecified or can be prespecified. In this way, a reliable seal and/or sealing effect and thus a constant quality can be achieved in the production of a plurality of dispensing devices in a simple manner. In addition, the method can be adapted to different sealing elements and can therefore be used flexibly.

The deformation value is preferably a measure of how much the sealing element is deformed. When the sealing element is deformed in the, in particular ring-shaped, receiving space, for example by a plunger, an in particular elastic deformation of the sealing element preferably takes place initially. During the deformation, the volume of the sealing element preferably remains at least approximately constant, and at least substantially only the outer geometric shape of the sealing element changes. With this deformation of the sealing element, the shape of the sealing element adapts to the shape of the receiving space and increasingly fills it out. This continues until the sealing element at least approximately completely fills the receiving space, and/or the shape of the sealing element corresponds at least approximately to the shape of the receiving space.

If the sealing element is now further deformed or compressed or is pressed in the receiving space, a volume compression of the sealing element preferably occurs. In contrast to (elastic) deformation, volume compression reduces the volume of the sealing element.

In summary, the behavior of the sealing element during deformation in the receiving space can be at least approximately divided into two phases, with substantially deformation occurring in the first phase at constant volume, while volume compression occurs in the second phase.

Of course, it cannot be ruled out that a (small) volume compression will already occur towards the end of the first phase and/or during the deformation.

The aforementioned threshold value, and/or threshold value for the deformation value—that is, the threshold value which is utilized for determining and/or selecting the assembly parameter—preferably corresponds to an onset of volume compression of the sealing element. In other words, the threshold value is preferably the value of the deformation value at which a volume compression of the sealing element begins. In this way, a reliable seal and/or sealing effect can be ensured. Furthermore, excessive wear or abrasion is prevented. This is conducive to consistent quality in the manufacture or assembly of a plurality of dispensing devices, in particular in an automated process.

The sealing element is particularly preferably deformed by the movement of a plunger and/or of the contact element or fixing element relative to the sealing element. The plunger can act on the contact and/or fixing element and thus indirectly move the contact and/or fixing element relative to the sealing element, and thus deform the sealing element via the contact and/or fixing element. However, it is also possible for the plunger to act directly on the sealing element and/or to deform the sealing element.

The movement of the plunger and/or contact element or fixing element relative to the sealing element preferably takes place in the axial and/or radial direction. In particular, the sealing element is arranged in the receiving space, such that the force or pressure exerted on the sealing element by means of the plunger and/or contact element or fixing element results in a deformation and/or compression of the sealing element in the receiving space.

In order to determine or examine the deformation behavior of each of the sealing elements, the force required in each case for the deformation is determined (directly or indirectly), in particular measured, for different deformations or deformation values of the sealing element. In this way, the force required for a specific deformation value can be determined. The force which is required for the deformation and which is determined or measured constitutes in particular a characteristic value from which the deformation value is or can be determined, calculated, or derived. Alternatively, the force causing the deformation can also be specified, and the deformation, and/or the travel path or axial position of the plunger and/or contact element or fixing element corresponding to the deformation, or in particular the height of the receiving space, can be determined, in particular measured.

As an alternative or in addition to determining or examining the deformation behavior of the sealing element, the friction behavior of the sealing element can also be determined and/or investigated, as already mentioned. To determine and/or investigate the friction behavior of each of the sealing elements, the sealing element and a boundary of the receiving space are preferably moved relative to one another, and the frictional force between the sealing element and the boundary is determined, in particular measured, in each case for different deformations or deformation values of the sealing element. The measured force preferably constitutes a characteristic value from which the deformation value is or can be determined, calculated, or derived. The boundary of the receiving space, which boundary is moved relative to the sealing element, is preferably the aforementioned central element which is guided through the receiving space and/or through the receptacle of the sealing element during the determination of the assembly parameter. In this case, the central element or the boundary is preferably moved axially with respect to the sealing element, in particular in an oscillating movement or a reciprocating movement. However, it is also possible for the sealing element to be rotated relative to the receiving space or the boundary, in particular the central element. In this case, the frictional force between the sealing element and the boundary is preferably a torsional frictional force. Accordingly, the characteristic value and/or the force measured to determine the deformation value is then preferably a torsion friction force.

At different points in time during the deformation, the sealing element is preferably deformed in each case to different extents in the receiving space. The different points in time therefore preferably correspond to different travel distances or positions of the fixing element and/or contact element.

In particular, a force/displacement curve is recorded to determine the deformation behavior and/or friction behavior and/or to determine the assembly parameter. The assembly parameter is preferably determined using the profile of the force/displacement curve. This is conducive to a simple, quick, and/or precise determination of the assembly parameter.

The force in the force/displacement curve is preferably the force used to deform the sealing element, and/or the frictional force between the sealing element and the boundary of the receiving space that is moved relative to the sealing element.

The displacement in the force/displacement curve is preferably the travel distance of the plunger or fixing element and/or contact element, or the height of the receiving space, or a displacement corresponding thereto.

The sealing element is preferably designed to seal a conveying element for conveying the medicament against a guide element which comprises or forms the receiving space and in which the conveying element is guided.

The sealing element is preferably ring-shaped, and/or a molded seal or a sealing ring, in particular an O-ring.

The sealing element is preferably a separate component that can be inserted into the receiving space. The sealing element preferably consists of an elastic material. An elastic material within the meaning of the invention is preferably a material with a modulus of elasticity of less than 100 MPa, preferably less than 50 MPa, in particular less than 10 MPa.

The sealing elements of different batches can consist of different materials and/or can have different deformation properties, different compression sets, and/or different creep behavior or different creep moduli. The method, in which an assembly parameter is determined separately for each batch, ensures that in each case a reliable seal and/or sealing effect is achieved even for such different sealing elements or batches of sealing elements. In particular, due to the precise adjustment of the volume of the receiving space that is possible with this method, materials can also be used for sealing elements which are partially plastic or have a comparatively high creep behavior—such as thermoplastic elastomers (TPE). Such sealing elements require receiving spaces that are particularly precisely designed or adapted to each of the sealing elements.

According to a further aspect that can also be implemented independently, the present invention relates to a dispensing device for dispensing a medicament. The dispensing device has a conveying element, in particular an axially movable conveying element, for conveying the medicament out of a container of the dispensing device, a guide element for guiding the conveying element, and an, in particular ring-shaped, sealing element for arrangement in a receiving space of the guide element. The sealing element is preferably designed to seal the conveying element against the guide element, in particular as a sealing ring. Furthermore, the sealing element can preferably be fixed in the receiving space by means of a fixing element and/or contact element that can be fastened to the guide element. The guide element preferably forms the pressure chamber of a piston pump, or the guide element comprises the pressure chamber, with the conveying element forming the piston of the piston pump.

The fixing element and/or contact element can preferably be fastened to the guide element in different axial positions relative to the guide element. As a result, it is possible and intended that the sealing element is or will be fixed with an adapted, specific assembly parameter. In this way, manufacturing tolerances and differences in size and/or material of sealing elements can be taken into account or compensated for in a simple manner, and a reliable seal and/or sealing effect can be ensured. This is conducive to consistent quality in the manufacture or assembly of a plurality of dispensing devices, in particular in an automated process.

The fixing and/or contact element can preferably be locked on the guide element in different axial positions relative to the guide element. This facilitates the correct or desired positioning of the fixing and/or contact element and is therefore conducive to simple and error-free assembly. This is conducive to consistent quality in the manufacture or assembly of a plurality of dispensing devices, in particular in an automated process.

Alternatively or additionally, the fixing and/or contact element and/or the guide element preferably has a positioning device for positioning the fixing and/or contact element relative to the guide element. The positioning device particularly preferably has one or more locking elements, in particular locking cams, or is formed from them. This is conducive to easier assembly and/or determination of the position of the fixing and/or contact element. As a result, manufacturing tolerances of sealing elements can be taken into account or compensated for in a simple manner, and a reliable seal and/or sealing effect can be ensured. This is conducive to consistent quality in the manufacture or assembly of a plurality of dispensing devices, in particular in an automated process.

The positioning device preferably has an inclined plane or helix structure or is formed therefrom. This is conducive to a simple adjustment of the position of the fixing and/or contact element relative to the guide element.

The positioning device is preferably arranged on the end face of the fixing and/or contact element and/or the guide element.

It is preferred that the rotational position of the fixing and/or contact element, in particular relative to the guide element or the dispensing device, defines the axial position of the fixing and/or contact element. In particular, the positioning device is designed accordingly.

A specific deformation or a specific deformation value of the sealing element and/or a size or a volume of the receiving space is preferably defined by the position of the fixing and/or contact element relative to the guide element, such that the deformation of the sealing element and/or the size or the volume of the receiving space can be varied or adapted to one another by varying the position of the fixing element.

The aforementioned and following aspects and features of the present invention can be combined with one another in different combinations, but can also be implemented independently of one another.

BRIEF DESCRIPTION OF THE DRAWING

Further aspects, features, advantages, and properties of the present invention are found in the claims and the following description of preferred embodiments, with reference to the drawings, in which:

Figure 1:
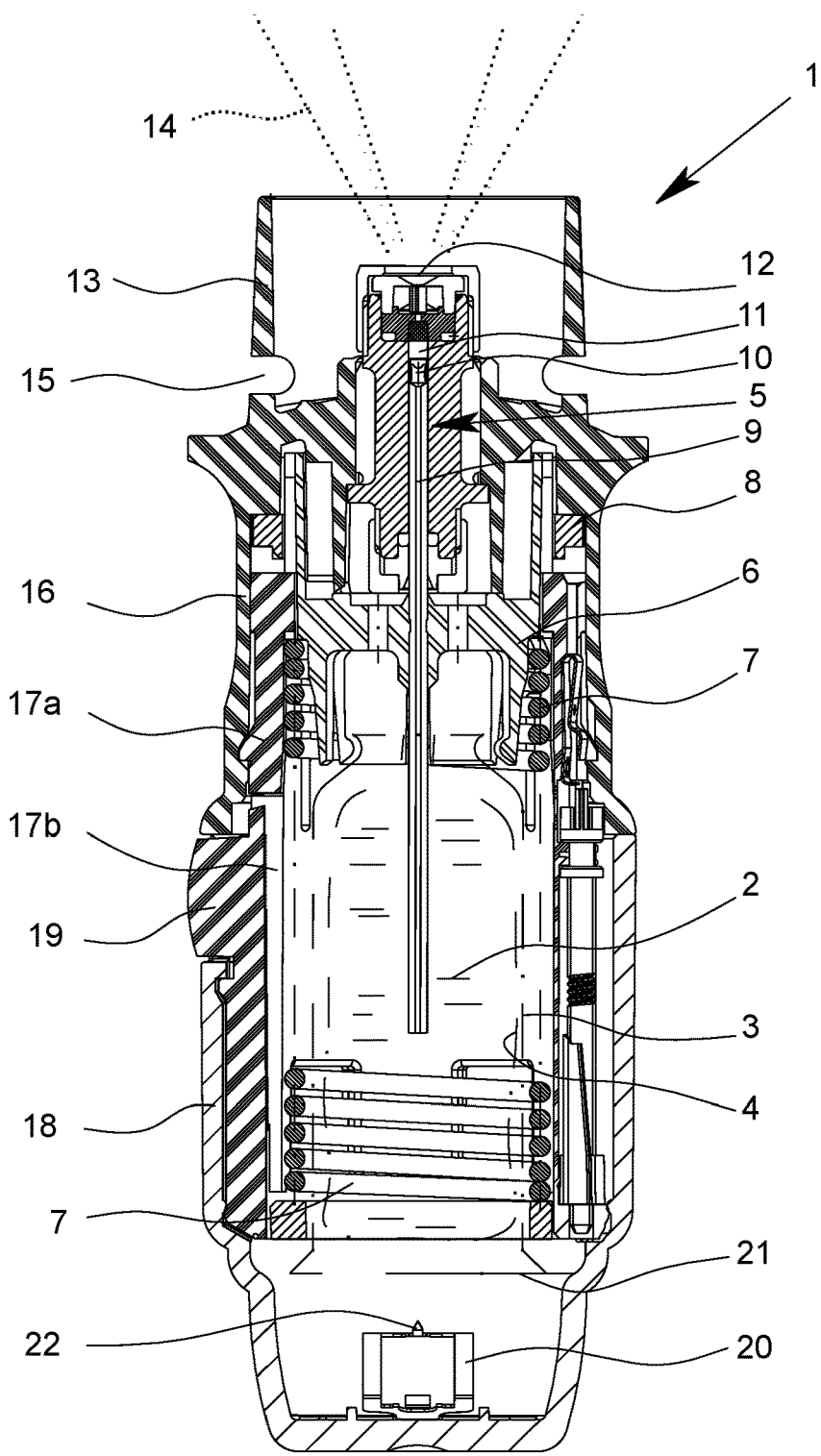
FIG. 1 is a schematic section of a dispensing device according to the invention in a first state.

In the drawings, some of which are not true to scale and are only schematic, the same reference signs are used for identical or similar parts. It is possible for corresponding or comparable properties and advantages to be achieved even if a repeated description is dispensed with for the sake of clarity.

DETAILED DESCRIPTION

Figure 2:
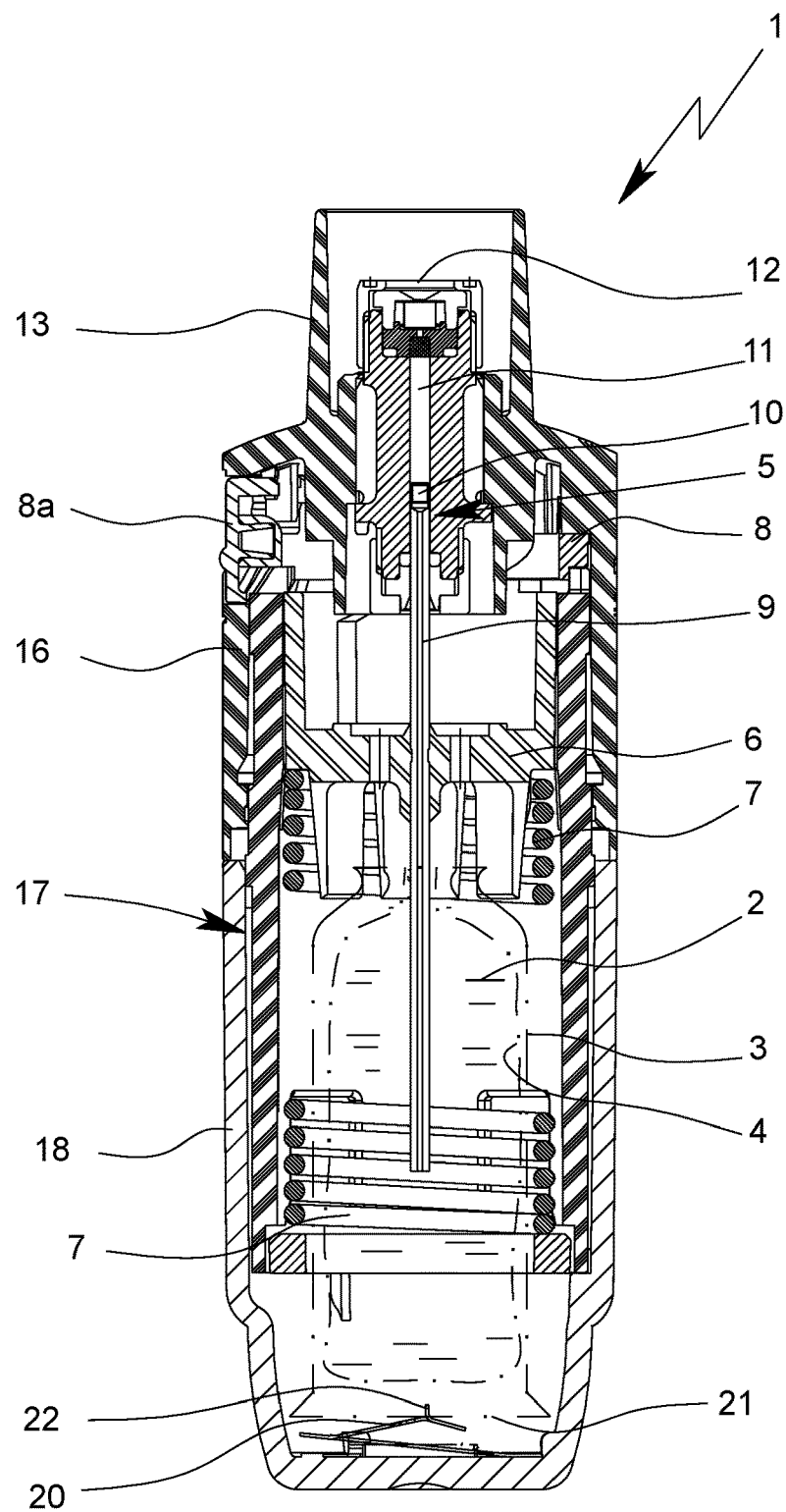
FIG. 2 is a schematic section, rotated by 90° compared to FIG. 1, of the dispensing device in a second state.

FIG. 1 and FIG. 2 show a proposed dispensing device 1 for dispensing a medicament 2. In particular, the dispensing device 1 is designed as a nebulizer and/or for nebulizing the medicament 2. The medicament 2 is preferably a fluid, in particular a liquid.

FIG. 1 shows the dispensing device 1 in a schematic sectional view in a first state, in this case in a non-ready-to-trigger state; FIG. 2 shows the same in a second state, in this case, in the ready-to-trigger state.

The dispensing device 1 is preferably designed as a carryable, portable, and/or mobile dispensing device 1.

When the medicament 2 is nebulized by means of the dispensing device 1, an aerosol 14 is preferably formed, in particular wherein the aerosol 14 can be breathed in or inhaled by a user, who is not shown. The dispensing device 1 is therefore preferably designed as an inhaler.

The inhalation usually takes place at least once a day, in particular several times a day, preferably at prespecified time intervals, for example depending on the patient's illness.

The aerosol 14 is preferably a particle/air mixture with solid and/or liquid particles, which are particularly preferably respirable—that is, in particular at least partially or on average smaller than 5 μm in diameter.

The dispensing device 1 is preferably free of propellant gas—that is, it preferably works without propellant gas. Instead, the dispensing device 1 preferably works with a mechanical pressure generator 5 and/or mechanism for generating the aerosol 14. In particular, it is a mechanically operated pump that places the medicament 2 under pressure, as a result of which the aerosol 14 is generated when it is discharged from a discharge nozzle 12. In principle, however, the dispensing device 1 can also be driven or operate in a different, preferably mechanical, manner.

The dispensing device 1 has a preferably insertable and preferably exchangeable container 3 with the substance and/or the medicament 2. The container 3 preferably forms a reservoir for the medicament 2 to be nebulized.

The container 3 preferably contains a sufficient amount of medicament 2 to be able to provide up to 200 dosage units, for example—that is to say, to allow up to 200 nebulizations or applications, for example. A typical container 3, as disclosed in WO 96/06011 A2 or in WO 00/49988 A2, has a volume of about 2 ml to 10 ml.

The container 3 is preferably at least substantially cylindrical or cartridge-like. In the example shown, it can be inserted into the dispensing device 1 from below and optionally exchanged after said dispensing device is opened. However, it can also be non-replaceable, and the dispensing device 1 can be disposable.

The container 3 is preferably at least substantially rigid. The container 3 is particularly preferably made of a plastics material, in particular a thermoplastic material, very particularly preferably polypropylene. The container 3 preferably has a flat surface on its base, or the container 3 has a flat container base 21.

The medicament 2 is preferably received in the container 3 in a fluid space 4 formed by a collapsible pouch.

The dispensing device 1 preferably also comprises the preferably mechanical pressure generator 5 for conveying and nebulizing the medicament 2, in each case in particular in a prespecified, optionally adjustable, dosage amount. The pressure generator 5 preferably forms a high-precision pump or dosing pump, in particular a piston pump.

The pressure generator 5 preferably has a drive spring 7, which is only partially shown in the example, for driving the pressure generator 5. The drive spring 7 is preferably designed to store energy, in particular mechanically, and to deliver it to the pressure generator 5, such that the pressure generator 5 pressurizes the medicament 2, as a result of which the aerosol 14 is formed from the medicament 2 when it is discharged from the discharge nozzle 12. The pressure generator 5 is therefore driven by the drive spring 7 or by the energy made available by the drive spring 7.

The pressure generator 5 preferably has a holder 6 for the container 3, for the associated drive unit, which is only partially shown, in particular in the form of the drive spring 7, and also for a particularly tubular conveying element 9, for a check valve 10, and/or for a pump chamber and/or pressure chamber 11.

The dispensing device 1 preferably has a clamping mechanism and/or locking element 8 which is designed to preferably automatically lock the drive spring 7 after an energy input into the drive spring 7. The energy input into the drive spring 7 preferably takes place by stretching, pulling, pushing, or, in particular, compressing the drive spring 7. For the sake of simplicity, this is summarized below with the term "tensioning" of the drive spring 7, and the state of the drive spring 7 thus achieved is assigned the attribute "tensioned" (regardless of whether the specific drive spring in the specific embodiment was stretched or compressed for this purpose). After tensioning or compression, the drive spring 7 is preferably kept in an energetically-higher and/or loaded or tensioned state by the locking element 8 which can in particular be actuated manually. The energy stored in the drive spring 7—in particular, by tensioning—is released and/or utilized by actuation of the locking element 8 (either directly, or preferably via a trigger button 8a) to generate pressure in the pressure generator 5.

The drive spring 7 is preferably a spiral or helical spring, wherein energy is stored or energy is introduced by means of axial compression of the drive spring 7.

The dispensing device 1 and/or the pressure generator 5 preferably has a discharge nozzle 12, in particular in the region of an optional mouthpiece 13.

The container 3 is preferably fixed in the dispensing device 1 or fluidically connected to the conveying element 9 via the holder 6, in particular in a locking manner, in such a way that the conveying element 9 dips into the container 3. The holder 6 can be designed in such a way that the container 3 can be detached and replaced.

When energy is input into the drive spring 7 and/or when the drive spring 7 is tensioned, the holder 6 is moved together with the container 3 and the conveying element 9 downwards in the illustrations (i.e., in the example shown, the drive spring 7 is axially compressed), and the medicament 2 is suctioned out of the container 3 via the check valve 10 into the pressure chamber 11 of the pressure generator 5.

During the subsequent unloading or relaxation of the drive spring 7 upon triggering by the actuation of the blocking element 8, the medicament 2 in the pressure chamber 11 is pressurized by the conveying element 9—with its now-closed check valve 10—being pushed upward and/or moved into the pressure chamber 11 by the drive spring 7, thereby serving as a plunger. This pressure expels the medicament 2 through the discharge nozzle 12, where it is nebulized to form the aerosol 14, as indicated in FIG. 1.

Since the conveying element 9 or the check valve 10 acts as a plunger, a movement of the conveying element 9 or the container 3 corresponds to a volume displaced in the pressure chamber 11 or to a discharged and/or dischargeable amount of medicament.

A user or patient, not shown, can inhale the nebulized medicament 2 and/or the aerosol 14, preferably wherein supply air can be suctioned into the mouthpiece 13 via at least one optional supply air opening 15.

In the illustrated example, the dispensing device 1 preferably has an upper housing part 16 and an inner part 17 (inner housing part) (cf. FIG. 2) which is rotatable relative thereto and which has an upper part 17a and a lower part 17b (cf. FIG. 1). A lower housing part 18, which can be actuated or rotated in particular manually, and/or a cap, is preferably fastened to, in particular fitted onto, the inner part 17 by means of a retaining element 19, in a detachable or non-detachable manner.

In order to insert and/or replace the container 3, the lower housing part 18 can preferably be detached from the dispensing device 1. However, the container 3 can also be non-replaceable.

The lower housing part 18 can be rotated against the upper housing part 16 or rotated relative to the upper housing part 16, preferably carrying along the lower part 17b of the inner part 17 in the illustration.

In particular, the lower housing part 18 is arranged on the inner part 17 in a rotationally fixed manner, preferably coupled to it with a positive fit. In this way, the inner part 17 can be rotated against the housing part 16 or rotated relative to the housing part 16 by means of the lower housing part 18. However, other solutions are also possible here.

As a result of the upper housing part 16 being rotated relative to the lower housing part 18 or the inner part 17, the drive spring 7 is loaded—in particular, compressed—in the axial direction via a gear mechanism (not shown) which acts on the holder 6. By clamping, the container 3 is preferably moved axially downwards until the container 3 assumes an end position indicated in FIG. 2. In this state, the drive spring 7 is loaded and/or the dispensing device 1 is ready for dispensing. During the nebulization process, the container 3 is preferably moved back (upwards) into its starting position by the drive spring 7.

The container 3 preferably performs an axial movement or lifting movement during the addition of energy and/or during the clamping process and/or for removing fluid and/or during the nebulization or dispensing of the medicament 2.

A ventilation opening of the container 3 is preferably opened when the drive spring 7 is loaded or tensioned for the first time. This is preferably done by means of a device which is preferably arranged in the housing part 18 and/or has a piercing element 22 for piercing the container 3 and/or a seal on the base of the container 3 for ventilation upon first contact. The piercing element 22 is preferably arranged on an axially acting spring 20 which comes into contact with the container base 21 when it is first loaded.

Figure 3:
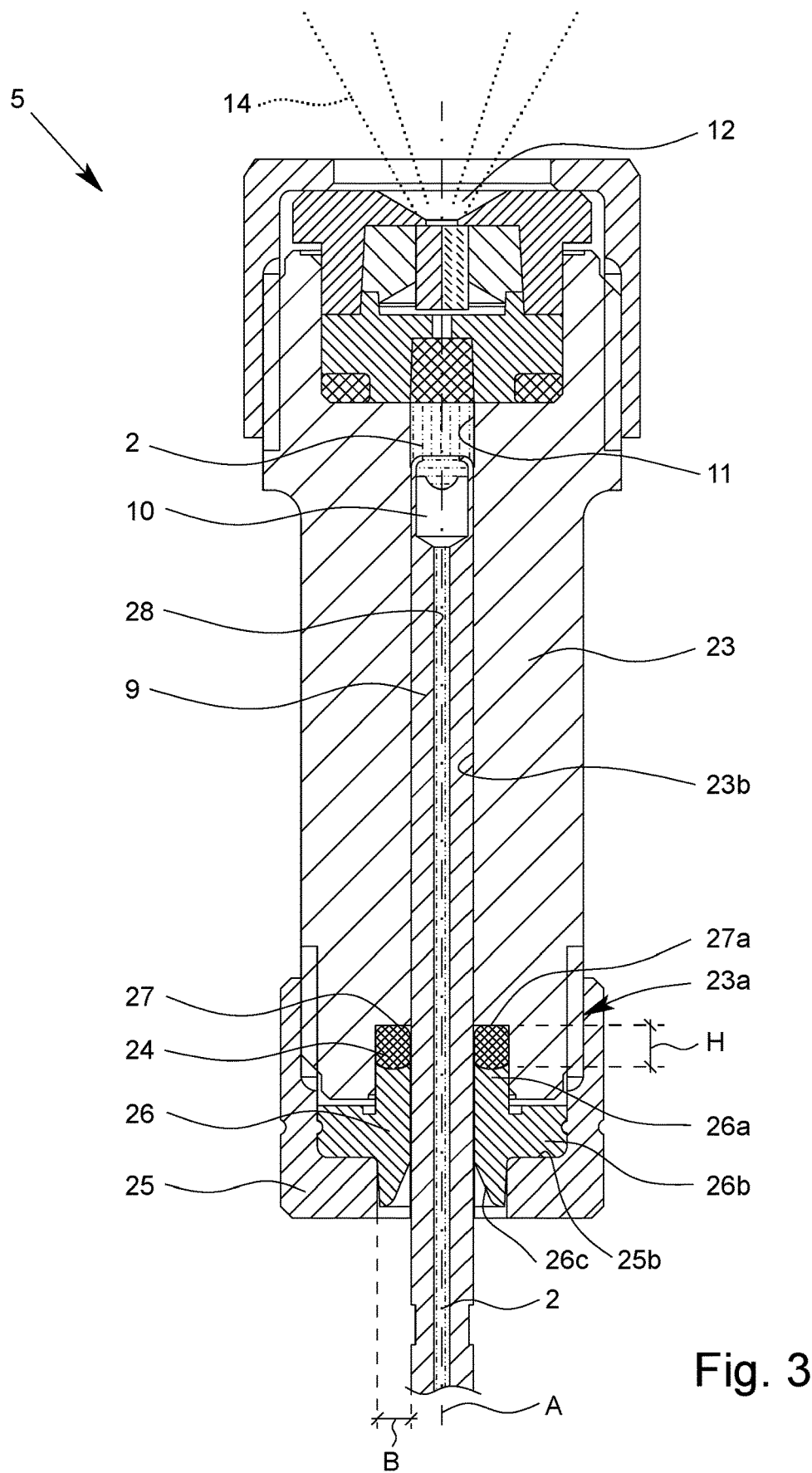
FIG. 3 is a schematic section of a pressure generator of the dispensing device.

In FIG. 3, the pressure generator 5 of the dispensing device 1 is shown in more detail, but schematically and not true to scale.

The dispensing device 1 and/or the pressure generator 5 is preferably designed to dispense, in particular to pump or dose, the medicament 2, preferably a liquid. The pressure generator 5 is particularly preferably designed as a piston pump. In particular, the dispensing device 1 and/or the pressure generator 5 is designed for very small pump volumes or dosages. In the example shown, the pump volume is preferably more than 1 µl, in particular more than 5 µl, and/or less than 1 ml, in particular less than 500 µl, particularly preferably less than 100 µl, very particularly preferably less than 30 µl, and in particular substantially 10 to 20 µl per piston stroke.

In order to be able to ensure precise conveying and dosing of the desired volume, in particular when the dispensing device 1 is actuated for the first time after a long period of non-use, it is necessary that no air enters the pressure generator 5, in particular when it is not in use. Otherwise, the dosing will no longer have the desired precision.

The dispensing device 1 and/or the pressure generator 5 preferably has an axis A. The axis A preferably corresponds to a primary axis, longitudinal axis, and/or axis of symmetry of the pressure generator 5 or conveying element 9 and/or the axis of movement of the conveying element 9. In particular, the pressure generator 5 extends substantially longitudinally along the axis A.

The designations "axial" and "radial" refer in particular to the axis A. An "axial" direction, extension, movement, or the like is therefore preferably parallel to the axis A, and a "radial" direction, extension, movement or the like is preferably radial to the axis A.

The dispensing device 1 and/or the pressure generator 5 preferably has a guide element 23 for guiding the conveying element 9, a sealing element 24, a receiving space 27 for receiving the sealing element 24, and in particular a fixing element 25 and/or contact element 26 for fixing or clamping and/or deforming the sealing element 24 in the receiving space 27.

In the (completely assembled) dispensing device 1, the sealing element 24 is arranged in the receiving space 27.

The fixing element 25 can preferably be fixed or fastened to the guide element 23, and/or fixed or fastened to the guide element 23 in the completely assembled dispensing device 1.

The fixing element 25 is preferably designed to fix or seat the sealing element 24 in the receiving space 27.

The contact element 26 is preferably designed for contacting the sealing element 24 and/or for being brought into contact with the sealing element 24. The contact element 26 preferably can be arranged or is arranged between the sealing element 24 and the fixing element 25.

The position of the contact element 26 can preferably be fixed or determined by means of the fixing element 25. The fixing element 25 can preferably also be fastened to the contact element 26, for example by crimping, screwing, gluing, welding, or the like. This is indicated in FIG. 3 by way of example.

In the example shown, the fixing element 25 and the contact element 26 are formed by two separate components.

The two-part design of the fixing element 25 and the contact element 26 has the advantage, for example, that the fixing element 25 and the contact element 26 can be better optimized for each of the requirements. For example, a particularly good fit with low tolerances in the receiving space 27 is important for the contact element 26 in order to reliably ensure a good seal. Therefore, the contact element 26 should have the least possible manufacturing tolerances which are less critical for the fixing element 25. The fixing element 25, on the other hand, can, for example, be optimized for a materially-bonded, positive, or non-positive connection with the pressure generator 5 or guide element 23 or another component—in particular, a component for fixing the axial position.

Furthermore, in one embodiment, the contact element 26 and the fixing element 25 can be produced as separate components from different materials. For example, the contact element 26 can be made of a more dimensionally stable and/or stiffer or harder material, and/or the fixing element 25 can be made of a softer or more ductile material, than the other component in each case. A "more ductile material" is in particular a material with greater ductility, the term "ductility" denoting the property of a material to permanently deform under shear stress before fracture—in particular to deform plastically. Overall, the flexibility in the manufacture and/or use of separate components is increased, and the manufacturing processes can be optimized.

A further advantage of designing the contact element 26 and the fixing element 25 as separate components is that the requirements for the components can be better met by selecting different materials for these components. A harder and/or more dimensionally stable material for the contact element 26 is preferred because this allows the sealing element 24 to be fixed permanently and/or consistently in the receiving space 27, and thus ensures a permanent and/or consistent seal by the sealing element 24. A softer and/or more ductile material for the fixing element 25 is preferred because this facilitates or allows a preferably deforming fastening of the fixing element 25 to the guide element 23, in particular by pressing or crimping. Overall, therefore, the choice of different materials for the contact element 26 and the fixing element 25 is advantageous for meeting the requirements.

However, it is also possible for the contact element 26 to be designed as a single piece with the fixing element 25 or vice versa, and/or for the contact element 26 to constitute or form a portion of the fixing element 25. Although the single-piece design leads to fewer components, it is only optional.

The guide element 23 is preferably designed as a guide tube and/or preferably forms an, in particular elongated and/or straight, channel 23b for receiving or guiding the conveying element 9 in a longitudinally displaceable manner. The conveying element 9 can preferably be arranged in the guide element 23 or, in the case of the completely assembled pressure generator 5 or dispensing device 1, is arranged or guided in the guide element 23. The conveying element 9 can preferably be moved relative to the guide element 23, in particular guided in a longitudinally or axially displaceable manner in the guide element 23 or the channel 23b.

The conveying element 9 preferably forms a piston, and/or the guide element 23 forms a cylinder and/or hollow cylinder. The guide element 23 and the conveying element 9 preferably together form a cylinder/piston arrangement, in particular a piston pump or a part thereof.

The conveying element 9 preferably delimits a pump space and/or the pressure chamber 11 in the guide element 23, as indicated in FIG. 3. The conveying element 9 is preferably provided with the check valve 10 which is arranged in particular on the end of the conveying element 9 facing the pressure chamber 11.

In the example shown, the preferably hollow conveying element 9 forms a supply channel 28 for the medicament 2 or comprises the supply channel 28. With a corresponding axial movement, the medicament 2 can be conveyed, in particular suctioned, through the supply channel 28 via the inlet valve or check valve 10 into the pressure chamber 11.

On the pressure or output side, the pressure generator 5 optionally has an outlet valve (not shown), and in particular the discharge nozzle 12, for dispensing and optionally nebulizing the medicament 2.

The pressure generator 5 according to the proposal or the dispensing device 1 according to the proposal is designed in particular as a nebulizer or inhaler in the example shown. The medicament 2 is alternately suctioned by the conveying element 9 through the supply channel 28 into the pressure chamber 11 with a corresponding axial reciprocating movement or is pressurized there and discharged via the discharge nozzle 12 and thereby administered, preferably nebulized. That is, a spray mist or aerosol 14 is formed from the medicament 2, as indicated in FIG. 3.

In the non-ready-to-trigger state, as shown in FIG. 1, the pressure chamber 11 is preferably reduced or minimized compared to the ready-to-trigger or loaded state shown in FIG. 2. In other words, the conveying element 9 and/or the piston preferably dips into the pressure chamber 11 when it is in the non-ready-to-trigger state. In the ready-to-trigger or loaded state, the conveying element 9 and/or the piston is preferably further away from the discharge nozzle 12 and/or is retracted from the pressure chamber 11, compared to the non-ready-to-trigger state shown in FIG. 1.

The dispensing device 1, and/or the pressure generator 5 and/or the guide element 23, preferably has the receiving space 27 for the sealing element 24 or forms or delimits it, in particular together with the contact element 26.

It is preferred that the guide element 23 (at least partially) has or forms the receiving space 27, or at least partially delimits it, in particular on the outside and/or on an axial end or end face which preferably faces the dispensing end and/or the pressure chamber 11 and/or the discharge nozzle 12.

If necessary, the receiving space 27 can also be formed separately from the guide element 23, preferably wherein the receiving space 27 and/or the component which has or which forms the receiving space 27 in this case is in contact with the guide element 23 or surrounds it.

The receiving space 27 is designed in particular as a recess in the guide element 23, particularly preferably as a groove or annular groove, an annular shoulder, or as a bushing.

The volume of the receiving space 27 is preferably decisively determined by the radial extension and/or width B of the receiving space 27 in the guide element 23 and the axial height H of the receiving space 27.

Preferably, the receiving space 27 is delimited at least partially by the guide element 23 and the contact element 26 and/or fixing element 25. The guide element 23 can form a cylindrical or hollow-cylindrical guide or receptacle for the contact element 26 and/or fixing element 25.

The receiving space 27 preferably surrounds the conveying element 9 radially and/or annularly.

The conveying element 9 preferably forms an inner radial boundary of the receiving space 27.

The guide element 23 preferably forms an axial and/or radial outer boundary for the receiving space 27.

In the illustrated example, the conveying element 9 has a circular cross section with a diameter of more than 0.25 mm, preferably more than 0.5 mm, in particular more than 0.75 mm and/or less than 4 mm, preferably less than 3 mm, in particular less than 2.25 mm.

The conveying element 9 is preferably made of metal, in particular stainless steel. It is designed in particular as a hollow element or capillary.

The conveying element 9 is preferably drawn, and accordingly has a relatively small tolerance with regard to its diameter.

The sealing element 24 is preferably at least partially deformable. The degree and/or the manner of a deformation of the sealing element 24 is preferably specified by a deformation value.

The sealing element 24 is preferably designed in the form of a continuous ring or as a molded seal or sealing ring—in particular, adapted to be received in the receiving space 27.

The sealing element 24 preferably has an opening 24a, in particular a central opening.

Figure 5A:
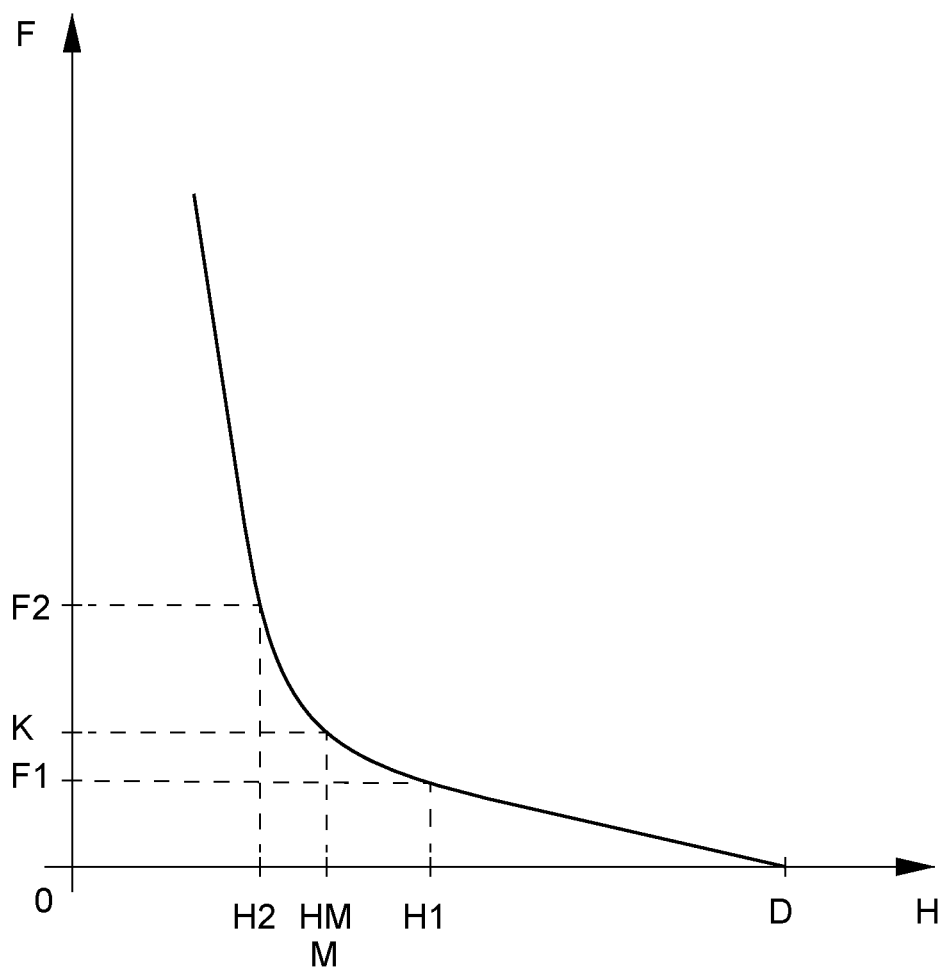
FIG. 5A is a schematic illustration of the profile of a measured value during a deformation and/or determination of an assembly parameter.
Figure 5B:
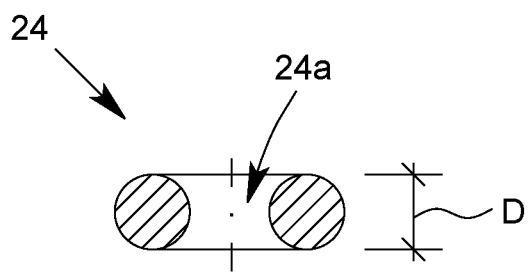
FIG. 5B is a schematic section of an undeformed sealing element.

In particular, the sealing element 24 is an O-ring with an at least substantially circular cross section in the non-installed or non-deformed state, as illustrated in FIG. 5B. However, the sealing element 24 can also be embodied as some other form of seal with, in particular, a non-circular cross section in the non-deformed state.

In the non-deformed state, the sealing element 24 preferably has a different cross section or a different volume than the receiving space 27 of the (completely assembled) dispensing device 1. The sealing element 24 is therefore preferably deformed during the assembly of the dispensing device 1, in particular when the contact element 26 and/or fixing element 25 is fastened to the guide element 23. Due to the deformation of the sealing element 24, an elastic tensioning of the sealing element 24 is produced, which is conducive to an optimal sealing effect of the sealing element 24 and/or which achieves or makes it possible to achieve a seal by means of the sealing element 24.

The deformation or the deformation value of the sealing element 24 is preferably not directly definable or adjustable, but rather is determined in particular by means of a characteristic value that correlates thereto, or is derived from a characteristic value. By using an assembly parameter M, it can be ensured in particular that the desired deformation of the sealing element 24 is achieved in the fully assembled dispensing device 1, and/or the deformation value of the sealing element 24 assumes the desired value.

The sealing elements 24 are preferably produced in batches—that is, in groups. In particular, a batch is produced from a specific amount of starting material that is as homogeneous as possible. The sealing elements 24 of a batch preferably have only a small variance and/or a high level of reproducibility with regard to their significant variables, such as ring diameter or effective ring diameter, cross section, volume, compressibility, or the like.

The volumes of the sealing elements 24 of a batch particularly preferably deviate by less than 10%, in particular less than 5%, particularly preferably less than 4% or 2%, from the mean volume or target volume of the sealing elements 24 of the batch.

In a specific example, the sealing elements 24 have a target volume or mean volume of more than 5 mm$^3$ and/or less than 10 mm$^3$, particularly preferably about 7 mm$^3$ to 8 mm$^3$, with all sealing elements 24 of the batch having a volume that deviates by at most 0.3 mm$^3$ from this target volume or mean volume.

The sealing elements 24 are preferably produced by injection molding, in particular by means of an injection molding tool (not shown) with a plurality of cavities. Accordingly, a plurality of sealing elements 24 is produced during each injection molding process.

The sealing element 24 is preferably an individual part and/or a separate component, in particular in the form of an O-ring or sealing ring. Alternatively, however, the sealing element 24 can also be formed directly on the guide element 23 or contact element 26, in particular by means of two-component injection molding. In this case, the batches would accordingly consist of guide elements 23 or contact elements 26 with sealing elements 24 formed therein or thereon, instead of just sealing elements 24, as explained above.

The sealing elements 24 can vary from batch to batch, in particular with regard to significant variables such as ring diameter or effective ring diameter, cross section, volume, compressibility, or the like. Variables like compressibility, which are determined by the material or the technical method, as well as quantities which are determined by the tools (ring diameter, thickness, volume, surface properties), are variable.

The sealing elements 24 of different batches preferably only differ in terms of manufacturing tolerances that arise as a result of production in different batches.

However, it is also possible that the sealing elements of different batches differ more significantly from one another and in particular have fundamentally different (nominal) dimensions, consist of different materials, have different deformation properties—for example, different moduli of compression, moduli of elasticity, compression hardness, and/or indentation hardness—and/or have different compression sets.

The sealing element 24 is preferably designed to seal off the conveying element 9 from the guide element 23, in particular in a gas-tight or diffusion-tight manner. In particular, the sealing element 24 is designed or arranged in such a way that no medicament 2 or fluid, in particular no gas and/or no liquid, can escape from the pressure chamber 11 and/or between the guide element 23 and the conveying element 9.

In the example shown, the cross section or the (effective) thickness D of the non-installed sealing element 24 is preferably more than 0.3 mm, in particular more than 0.5 mm, particularly preferably 1 mm or more, and/or less than 3 mm, less than 2 mm, more preferably less than 1.5 mm. The inner diameter or the size of the central opening 24a of the sealing element 24 preferably corresponds approximately to the outer diameter of the conveying element 9.

The sealing element 24 preferably consists of an elastic material. An elastic material within the meaning of the invention is preferably a material with a modulus of elasticity of less than 100 MPa, preferably less than 50 MPa, in particular less than 10 MPa.

The sealing element 24 preferably consists of a rubber-elastic material or natural rubber suitable for pharmaceuticals or food. The sealing element 24 is preferably made of silicone, fluorinated rubber (FKM), a thermoplastic elastomer (TPE), ethylene-propylene-diene rubber (EPDM), chloro-isobutene-isoprene rubber or chlorobutyl rubber (CIIR), bromobutyl rubber (BIIR), polyurethane (PUR), and/or nitrile rubber (NBR).

Different materials which can be considered for the sealing element 24 have different properties. On the one hand, there are materials that have an increased leakage rate and/or reduced diffusion tightness when they come into contact with a pharmaceutical at elevated temperature and/or at elevated pressure. In other words, it is therefore possible that, upon contact with a pharmaceutical or at elevated temperature or elevated pressure, the sealing effect of the sealing element 24 is reduced because there is increased diffusion through the sealing element 24.

With a sealing element 24 consisting of such a material, static sealing or good storage tightness is made more difficult by the fact that substances can diffuse through the sealing material or sealing element 24. In this case, the diffusion loss is preferably in particular proportional to the size of the free surface and/or inversely proportional to the extension of the sealing element 24 in the direction of diffusion.

Furthermore, there are materials in which the contact stress on the sealing surfaces of the sealing element 24—that is, in particular the surfaces that are in contact with the boundary of the receiving space 27—decreases at an increased temperature and/or an increased pressure. In other words, creep of the material or sealing element 24 is observed with these materials under increased pressure and/or increased temperature.

In this case, a storage leak and/or poor static seal occurs, in particular because if the compressive stress of the sealing material or sealing element 24 on the counter surface—in the present case, in particular the surface of the conveying element 9—is too low, the roughness or microporosity of the surface causes a leak.

The problem with the sealing of the conveying element 9 by the sealing element 24 is therefore, in particular, to meet two effectively competing requirements. On the one hand a high tensioning pressure or a strong deformation of the sealing element 24 in the receiving space 27 is desirable, or is advantageous to the extent that a storage leak is avoided, and/or the static sealing can be improved. On the other hand, however, a high preload pressure or severe deformation of the sealing element 24 means that the dynamic seal—that is, the sealing of the conveying element 9 deteriorates during a movement of the conveying element 9 relative to the sealing element 24, since creep and/or flow of the material is increased with an increased preload pressure and the abrasion due to the relative movement between the conveying element 9 and the sealing element 24 is also increased. In addition, too high a preload pressure not only leads to increased abrasion but also to more difficult operation or movement of the conveying element 9. This can lead to the conveying element 9 not moving or not moving as intended, such that, for example, too small a dose of the medicament 2 is discharged in a delivery stroke and/or insufficient nebulization takes place.

In particular, the deformation value is a measure of how much the sealing element 24 is deformed and/or what the ratio is between the cross section or volume of the (deformed) sealing element 24 and the cross section or volume of the receiving space 27 in the completely assembled dispensing device 1. The deformation value is therefore in particular a measure of how strong the elastic tensioning of the sealing element 24 is in the receiving space 27.

The sealing element 24 should in particular be deformed in such a way, and/or the deformation value of the sealing element 24 should be selected or adjusted in such a way, that the aforementioned competing requirements are met as optimally as possible. On the one hand, the deformation should be sufficiently high that there is an elastic tensioning in the sealing element 24, and as a result, a storage leak can be prevented. On the other hand, the deformation should be sufficiently low that a good dynamic seal is ensured, and/or flow and/or creep of the material is prevented.

The proposed method for installing the sealing element 24, and the proposed dispensing device 1, are intended in particular to ensure that the sealing element 24 is arranged in the receiving space 27 or is fixed in the receiving space 27 with a preload pressure that allows both a good static seal and a dynamic seal to be implemented or achieved. Furthermore, the proposed method is preferably suitable for a large number of materials and/or different materials.

In the assembled state—that is to say, with the pressure generator 5 installed—the sealing element 24 is at least substantially received in the receiving space 27, as illustrated in FIG. 3. The contact element 26 or fixing element 25 preferably rests axially on the sealing element 24 and fixes the sealing element 24 axially in the receiving space 27. Furthermore, the sealing element 24 is preferably in radial and sealing contact with the conveying element 9, which itself passes through the sealing element 24. The sealing element 24 is in particular clamped or compressed in the receiving space 27—that is, deformed—in the installed state. In the installed state, the sealing element 24 preferably has a substantially rectangular shape in cross section, or at least one flat contact side facing the conveying element 9.

In order to be able to achieve a good seal and correspondingly precise dosing, the desired degree of filling—that is, the "target degree of filling," is on average preferably more than 90%, in particular more than 95%, and/or less than 110%, in particular less than 105%, particularly preferably at least substantially 100%, in particular with a tolerance of 4%, 2%, or less.

The "degree of filling" corresponds to the ratio of the volume of the undeformed sealing element 24 (as shown in particular in FIG. 5B) divided by the volume of the receiving space 27. The method according to the invention and the proposed dispensing device 1 are preferably designed to implement or reproduce this or any other desired degree of filling.

The volume of the receiving space 27 can preferably be adjusted and/or fixed in a variable manner and/or by or during assembly.

In the illustrated example, the contact element 26 is preferably fixed or fastened to the guide element 23 by the fixing element 25—in particular, in its position in which it is axially tensioned against the sealing element 24. A defined position of the contact element 26 and thus a defined axial length or height H of the receiving space 27 for the sealing element 24 can be achieved by means of corresponding axial and/or end-face contact surfaces.

The height H of the receiving space 27 is in particular the (axial) spacing between a base 27a or the annular surface or annular shoulder of the receiving space 27 formed by the guide element 23 and the end face of the contact element 26 facing the base 27a and/or sealing element 24, and/or the end face of a contact portion 26a of the contact element 26, as indicated in FIG. 3.

The fixing element 25 is preferably designed in the manner of a cap, and/or it overlaps the contact element 26 on an end face or on the free end.

The contact element 26 is preferably at least substantially ring-shaped. The contact element preferably has a central opening. The diameter of the central opening preferably corresponds to the diameter of the channel 23b, or the diameter of the central opening is greater than the diameter of the channel 23b and/or the conveying element 9.

The contact element 26 preferably has a contact portion 26a which is designed for direct contact with the sealing element 24. The contact portion 26a is formed in particular by a portion of the contact element 26 at the axial end. In the completely assembled dispensing device 1, the contact portion 26a preferably contacts the sealing element 24, and/or the contact portion 26a fixes the sealing element 24 in the receiving space 27, or the contact portion 26a clamps the sealing element 24a in the receiving space 27.

The end face of the contact portion 26a facing the sealing element 24 is preferably curved in the radial direction and/or adapted to the shape of the sealing ring or sealing element 24. In this way, the dead space, in particular the region of the receiving space 27 that is not filled by the sealing element 24, can be reduced or minimized. The contact portion 26a preferably has a sealing lip facing the sealing element 24. The sealing lip preferably serves as an extrusion barrier and/or is designed to prevent the sealing element 24 from creeping into the channel 23b.

The contact portion 26a is preferably ring-shaped in cross section (that is, in the section perpendicular to the axis A)—in particular in the form of a circular ring.

The contact element 26 preferably has a contact surface and/or a stop 26b for the fixing element 25. In particular, the stop 26b is formed by an annular shoulder or a flange of the fixing element 25.

The fixing element 25 preferably has a counter surface 25a assigned to the stop 26b in order to contact the stop 26b and/or to hold or fix the stop 26b and thus the contact element 26 axially.

The contact element 26 preferably has a particularly conical insertion portion 26c through which the insertion of the conveying element 9 into the contact element 26 is facilitated. Alternatively or additionally, the insertion of a plunger 29 or a central element 30 during a determination of an assembly parameter M is also facilitated by the insertion portion 26c. The insertion portion 26c preferably has a bevel and/or rounding, or is formed therefrom. In particular, a central opening of the contact element 26 is radially widened or enlarged by the insertion portion 26c and/or the bevel/rounding towards the free end of the contact element 26.

The position, in particular the axial position, of the fixing element 25 is preferably variable. The fixing element 25 can preferably be fastened to the guide element 23 in different, in particular axial, positions relative to the guide element 23. For this purpose, the guide element 23 preferably has a fastening portion 23a. The fastening portion 23a is preferably arranged or formed on a peripheral side of the guide element 23.

In the example shown in FIG. 4, the fastening portion 23a preferably has one or more engagement options, such as recesses 23c or a threading. However, the fastening portion 23a can also have a different design—for example, it can have an adhesive surface or be formed by it.

The fixing element 25 and/or contact element 26 can preferably be fastened to the guide element 23 in various discrete positions relative to the guide element 23. A "discrete position" within the meaning of the present invention is in particular a position that is defined or fixed by the geometric shape of the fixing element 25, the contact element 26, and/or the guide element 23 and/or fastening portion 23a.

Figure 4A:
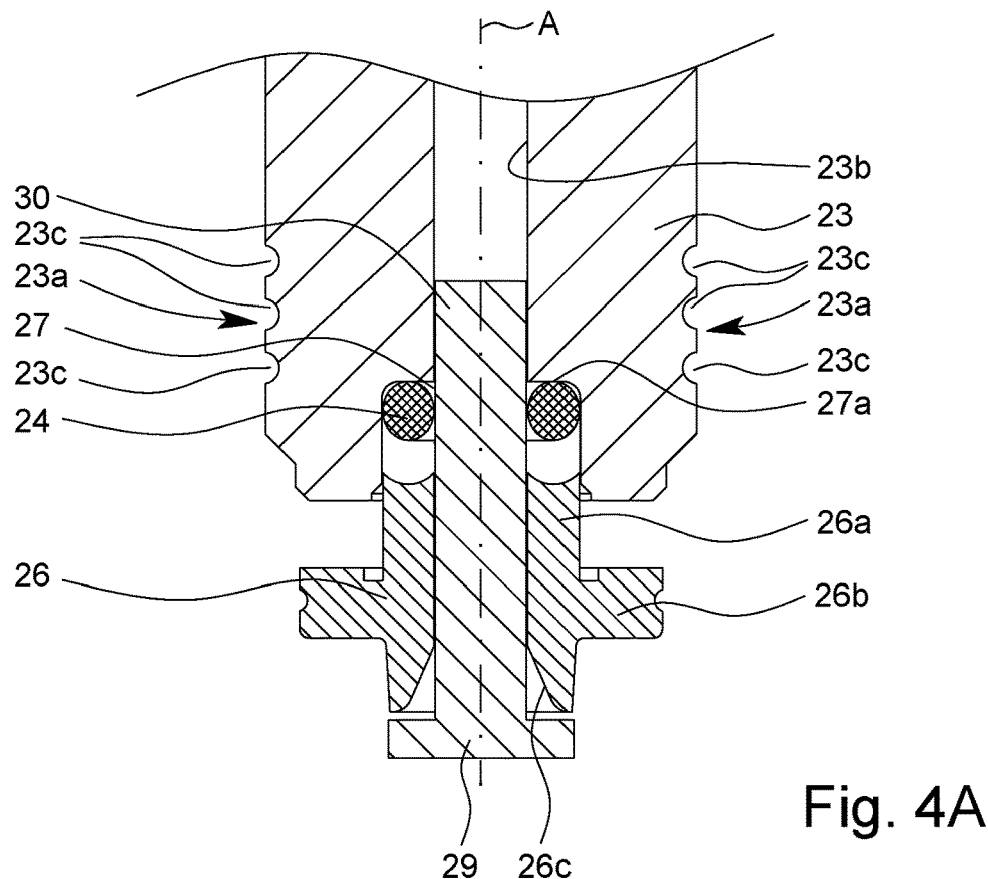
FIG. 4A is a schematic section of the pressure generator during a first situation in a determination of the assembly parameter.
Figure 4B:
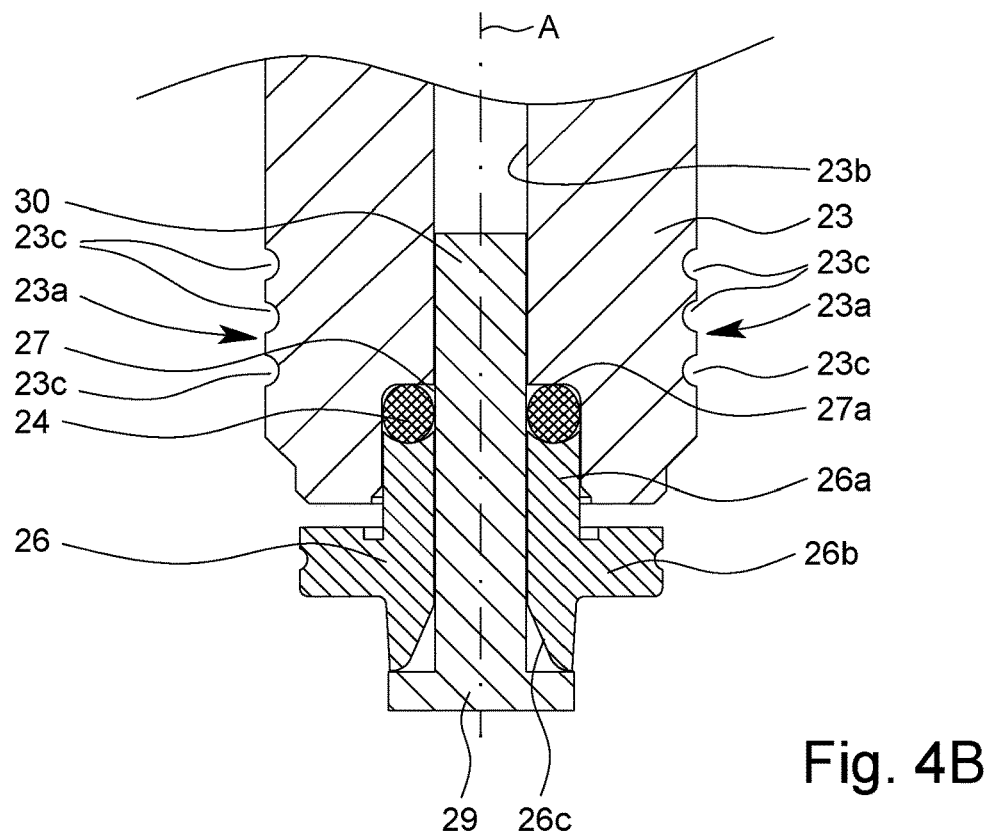
FIG. 4B is a schematic section of the pressure generator during a second situation in a determination of the assembly parameter.
Figure 4C:
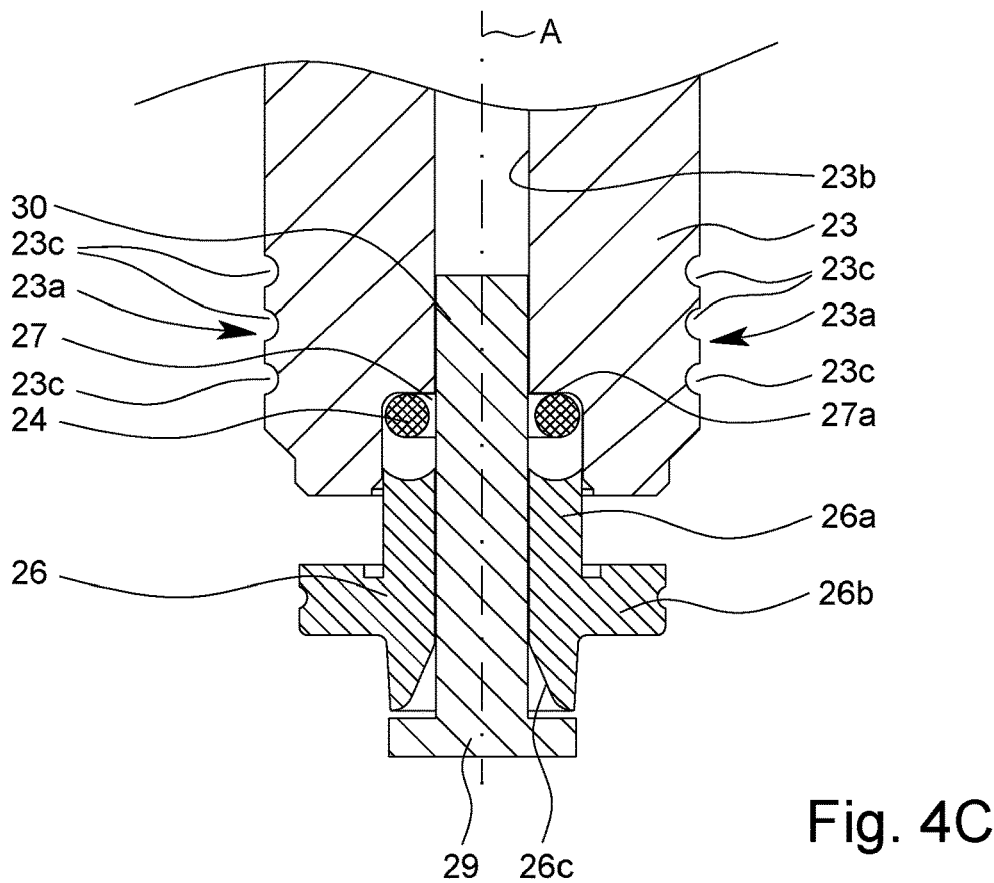
FIG. 4C is a schematic section of the pressure generator according to FIG. 4A during the first situation in the determination of the assembly parameter, the sealing element having a different size than in FIG. 4A.
Figure 4D:
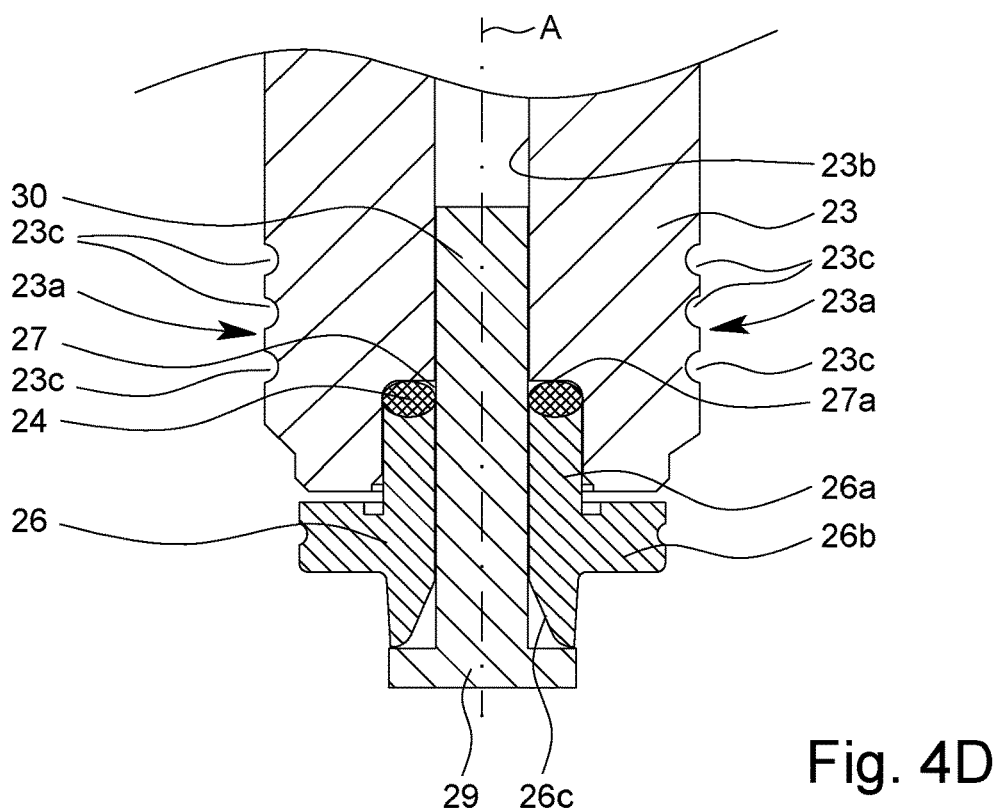
FIG. 4D is a schematic section of the pressure generator according to FIG. 4C during the second situation in a determination of the assembly parameter.
Figure 4E:
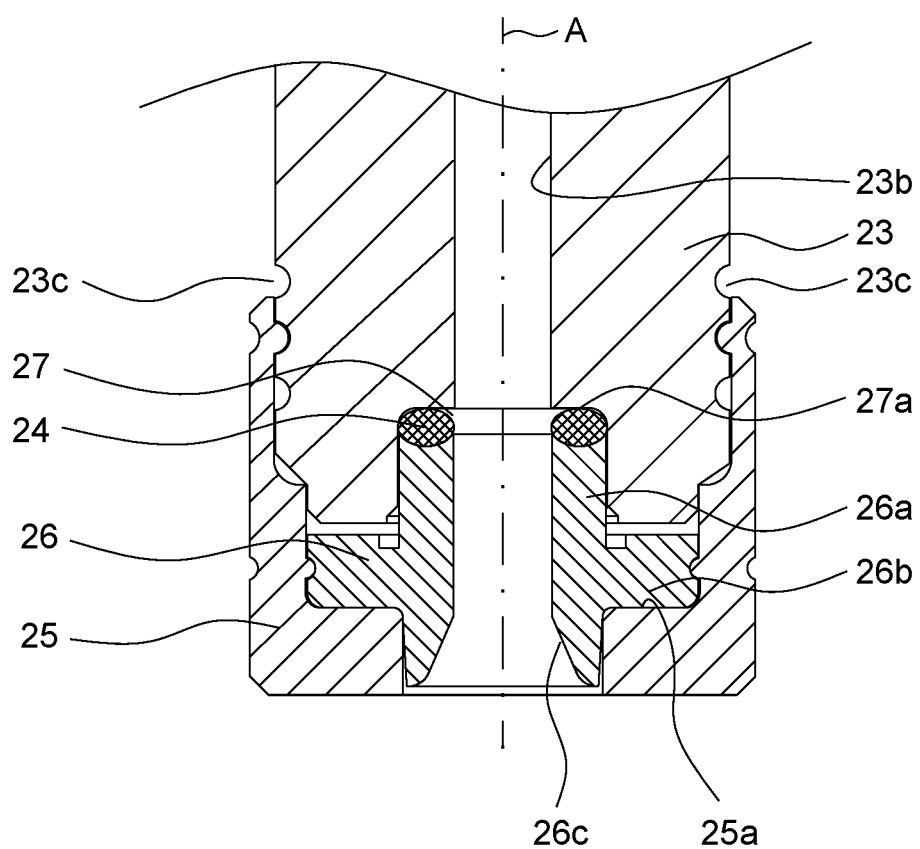
FIG. 4E is a schematic section of the pressure generator after fixing the sealing element.

The fixing element 25 is fixed, for example, by screwing or gluing, as indicated in FIG. 3, or, for example, by deformation, in particular at the same time forming one or a plurality of seams, and/or can be fastened to the guide element 23 by engaging in particular radially, preferably in one or more recesses 23c of the guide element 23, as indicated in FIG. 4E. In particular, the guide element 23 and/or the fastening portion 23a can have a plurality of recesses 23c which are arranged at different axial positions.

In particular, a plurality of discrete positions of the fixing element 25 and/or contact element 26 relative to the guide element 23 is defined or implemented by the plurality of recesses 23c. In other words, the fixing element 25 and/or contact element 26 can be fastened to the guide element 23 in various discrete positions relative to the guide element 23, preferably through the recesses 23c. In particular, the axial position of the fixing element 25 and/or contact element 26, and thus the height H and ultimately the volume of the receiving space 27, can be adjusted or varied.

In other words, it is preferable for the fixing element 25 to be fastened in a fixed or defined position on the guide element 23 and/or the fastening portion 23a in the fully assembled dispensing device 1, and/or for the fixing element 25 and/or contact element 26 to be fixed in a fixed and/or unchangeable position relative to the guide element 23, wherein, however, it is possible for different, in particular axial and/or discrete, positions relative to the guide element 23 to be selected and/or implemented during the fixing and/or fastening of the fixing element 25 and/or contact element 26. In this way, in particular, the volume of the receiving space 27 and/or the ratio of the volume of the receiving space 27 to the volume of the sealing element 24 can be selected and/or adapted to the sealing element 24. The ability to vary the position of the fixing element 25 and/or contact element 26 during assembly forms in particular an aspect of the present invention that can be implemented independently.

In particular, the position of the fixing element 25 and/or contact element 26 defines a deformation of the sealing element 24 and/or a size or a volume of the receiving space 27, such that the deformation of the sealing element 24 and/or the size or the volume of the receiving space 27 can be varied by varying the position of the fixing element 25 and/or contact element 26.

There are preferably various options for fastening the fixing element 25 to the guide element 23. The fixing element 25 can be fastened to the guide element 23 in a non-positive, positive, and/or materially-bonded manner.

Preferred options for fastening the fixing element 25 are screwing the fixing element 25, (positive) fastening using pins, primary shaping fastening (e.g., molding, or material bonding using a curable resin, in particular using UV-curable resin, and/or an adhesive), fastening by forming (e.g., crimping or heat caulking), fastening by machining, welding, soldering, or the like.

According to one example, the fixing element 25 can be designed as a nut or union nut and can be fastened to the guide element 23 in the position specified by the assembly parameter M by screwing, in particular with a defined torque. The threads used in this case are preferably designed as coarse threads, and/or with no self-locking function. This is indicated by way of example in FIG. 3.

According to a further example, the fixing element 25 can be designed as a crimp sleeve and can be crimped firmly in the position specified by the assembly parameter M on the guide element 23 and/or the fastening portion 23a.

For this purpose, the guide element 23 can have one or more recesses 23c or be formed by them. The recesses 23c are preferably arranged on the outside of the guide element 23. In particular, the recesses 23c correspond to different (axial) and/or discrete positions of the fixing element 25 and/or the recesses 23c define different axial and/or discrete positions of the fixing element 25 and/or contact element 26. This is indicated by way of example in FIG. 4A—FIG. 4E.

The recesses 23c are preferably designed as grooves or seams. The recesses 23c, in particular grooves or seams, can be continuous, and/or the guide element 23 can be formed completely around the circumference, and/or can be formed in the circumferential direction by a plurality of recesses 23c that are separate from one another.

In the embodiment with a plurality of recesses 23c, illustrated in FIG. 4A—FIG. 4E, the fixing element 25 can preferably be fastened or fixed on the guide element 23 in various discrete positions, which in particular correspond to individual recesses 23c.

Alternatively or additionally, only one or precisely one such recess 23c or groove or seam can be provided, wherein a plurality of crimp sleeves having different axial lengths are provided, such that different assembly parameters M correspond to different fixing elements 25 and/or crimp sleeves having different axial lengths and/or are implemented by different fixing elements 25.

The fixing element 25 can be preformed for engaging with a recess 23c, for example by the fixing element 25 having a peripheral edge or an edge designed to correspond in some other way to the recess 23c, for engaging with the recess 23c. However, this is not mandatory. A discrete position of the fixing element 25 and/or contact element 26 is also defined by such a deformation of the fixing element 25, in combination with the recesses 23c. It is also possible that the fixing element 25 does not have such a preformed shape, and rather only the guide element 23 and/or the fastening portion 23a has one or more recesses 23c, wherein the fixing element 25 is continuously displaceable relative to the guide element 23 and/or the fastening portion 23a, and a deformation tool deforms the fixing element 25 into the recess 23c in order to fasten or fix the fixing element 25.

According to a further example, the fixing element 25 can be fixed by gluing or welding to the guide element 23 in the position specified by the assembly parameter M—in particular, by laser welding, ultrasonic welding, and/or friction welding.

Optionally, the fixing element 25 can be fastened to the contact element 26, in which case the fastening element 25 can be fastened to the contact element 26 in the same way as the fastening element 25 is fastened to the guide element 23. The above statements regarding the fastening of the fixing element 25 to the guide element 23 therefore apply analogously to the fastening of the fixing element 25 to the contact element 26. A firm connection between the contact element 26 and the fixing element 25 is preferably produced only after the contact element 26 has been positioned.

In the embodiment illustrated in FIG. 4E, the contact element 26 or its stop 26b has a groove or seam on the radial outside, and the fixing element 25 is deformed by crimping into this groove or seam or being fastened to the contact element 26.

Figure 6:
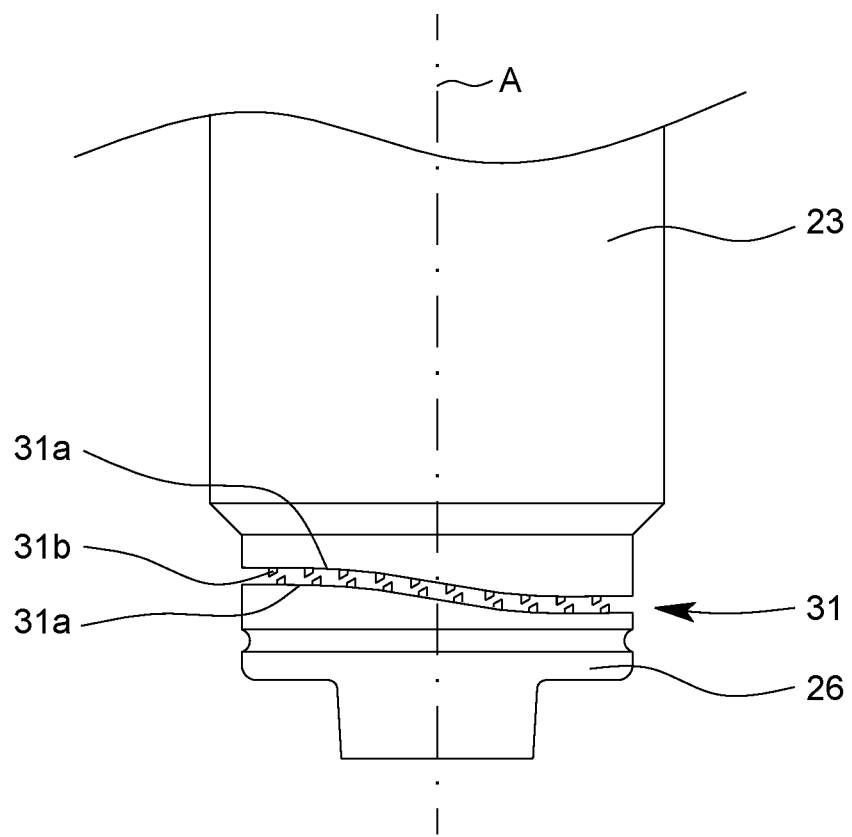
FIG. 6 is a schematic side view of the pressure generator according to a further embodiment.

FIG. 6 schematically shows part of the dispensing device 1 and/or of the pressure generator 5 according to a further preferred embodiment. FIG. 6 shows a side view of the pressure generator 5 shown in a sectional view in FIG. 4E, with the fixing element 25 being omitted and only the contact element 26 and the guide element 23 being shown.

According to the embodiment shown in FIG. 6, the fixing and/or contact element 25, 26 can preferably be locked in different axial and/or discrete positions on the guide element 23 relative to the guide element 23. In particular, different discrete positions of the fixing element and/or contact element 25, 26 relative to the guide element 23 are defined or can be defined in this way.

Preferably, the fixing and/or contact element 25, 26 and/or the guide element 23 has a positioning device 31 for positioning the fixing and/or contact element 25, 26 relative to the guide element 23. The positioning device 31 is preferably formed by mutually corresponding surfaces or portions of the contact element 26 and the guide element 23, or has such surfaces.

The positioning device 31 is preferably arranged on an end face of the contact element 26 assigned to or facing the guide element 23, and/or on an end face of the guide element 23 assigned to or facing the contact element 26.

In the example shown, the positioning device 31 is formed in particular by one or more helix structures 31a, or comprises them. Both the contact element 26 and the guide element 23 preferably comprise a helix structure 31a.

The (in particular axial) position of the contact element 26 relative to the guide element 23 can preferably be adjusted or varied by means of the helix structure 31a. In particular, the position of the contact element 26 relative to the guide element 23 can be changed by rotating the contact element 26 about the axis A or by rotating the contact element 26 relative to the guide element 23. During such a rotation, the helix structures 31a of the contact element 26 and the guide element 23 preferably slide along each other, and thus change the axial position of the guide element 23 and contact element 26 relative to one another.

However, instead of the helix structure 31a, it is possible to only provide an inclined plane or inclined surface, or the like.

Preferably, the axial position of the fixing element 25 and/or contact element 26, in particular relative to the guide element 23, is fixed or can be fixed by the rotational position of the fixing element 25 and/or contact element 26. This is preferably made possible or implemented by the positioning device 31, in particular by the inclined plane or inclined surface or helix structure 31a.

The positioning device 31 preferably has one or more locking elements 31b, or is formed by them. In particular, the contact element 26 can be locked on the guide element 23 in a (defined) axial position relative to the guide element 23 by the locking elements 31b.

The contact element 26 and the guide element 23 preferably have locking elements 31b which correspond to one another.

In particular, the locking elements 31b of the contact element 26 and the guide element 23 are designed to engage or interact with one another.

The locking elements 31b are particularly preferably designed in such a way that a rotation of the contact element 26 relative to the guide element 23 is only possible in one direction of rotation about the axis A, and a rotation in a direction opposite to this direction of rotation is prevented. As shown in FIG. 6, this can be done by appropriately designing the locking elements 31B with sloping and vertical surfaces.

When the contact element 26 is locked into the guide element 23 and/or after the dispensing device 1 has been assembled, the positioning devices 31, helix structures 31a, and/or locking elements 31b of the contact element 26 and guide element 23 are preferably in contact and/or rest against one another. A spacing between the contact element 26 and the guide element 23 is shown in FIG. 6 merely for the sake of clarity.

The positioning device 31, in particular the inclined planes or helix structures 31a and/or locking elements 31b, preferably defines various discrete positions of the fixing element and/or contact element 25, 26 relative to the guide element 23. In other words, the positioning device 31, in particular the inclined planes or helix structures 31a and/or locking elements 31b, can be used to fasten, in particular lock, the fixing element 25 and/or contact element 26 on the guide element 23 in various discrete positions relative to the guide element 23. Proposed methods for assembling the dispensing device 1 or for assembling (a plurality of) dispensing devices 1 are discussed in particular below.

In particular, an assembly method in which sealing elements 24 are present in batches will be described first below. In this case, the variance with regard to the significant dimensions of the sealing elements 24 is preferably low within a batch. In this method, an assembly parameter M is preferably first determined using a random sample of a small number of sealing elements 24 of the batch, and this assembly parameter M is then later used for each sealing element 24 during the installation of the sealing elements 24 of the batch. In particular, the assembly parameter M is determined (batch by batch) before or independently of the actual installation of the sealing elements 24. This method will be referred to in particular as the batch method.

In a further assembly method which will be described after the batch method, an assembly parameter M is preferably determined individually or separately for each sealing element 24 to be installed, and the sealing element 24 is installed using this assembly parameter M. In particular, the installation or fixation of the sealing element 24 takes place during or immediately after the determination of the assembly parameter M. In this method, the sealing elements 24 can differ from each other more in terms of their significant dimensions, and/or can come from different batches. Nevertheless, this method can also be applied to sealing elements 24 that are available in batches and have a low variance with regard to the significant dimensions. This method is referred to in particular as the individual method.

First, however, the batch method will be discussed in more detail.

An assembly parameter M is preferably determined separately for each batch of sealing elements 24. The procedure for determining the assembly parameter M will be described in more detail below after an overview of the entire batch method has been given.

A batch preferably has a plurality of sealing elements 24, preferably more than 10,000, preferably more than 100,000, in particular more than 200,000, sealing elements 24, and/or less than 1,000,000, in particular less than 800,000, sealing elements 24.

The assembly parameter M is preferably determined using a random sample or subset of sealing elements 24 of the batch.

In particular, the random sample has a small number, preferably at least 10, preferably at least 50, in particular at least 80 and/or at most 250, preferably at most 150, in particular at most 125, of sealing elements 24 of the batch.

Preferably, the size of the random sample depends on the size of the batch, in particular using larger random samples for larger batches.

The random sample preferably has less than 50‰, preferably less than 20‰, in particular less than 10‰, particularly preferably less than 5‰, very particularly preferably less than 2‰ of the sealing elements 24 of the batch.

The assembly parameter M or its value is preferably determined separately from the actual assembly of the sealing elements 24 or the dispensing device(s) 1, in particular in a test system (not shown).

The receiving space 27 of the test system preferably has the same dimensions as the receiving space 27 of the dispensing device 1. However, for the sake of simplicity, the method is described below with reference to a receiving space 27 of the dispensing device 1.

Likewise, the contact element does not have to be a contact element 26 of the dispensing device 1, but can also be formed by a test element of the test system. In this case, the test element is preferably designed similarly or identically to the contact element 26.

The test system preferably does not have a complete dispensing device 1 and/or a complete pressure generator 5, but rather only a receiving space 27 with the same dimensions as the receiving space 27 of the dispensing device 1 and/or of the pressure generator 5. The receiving space of the test system is preferably also made of the same material as the receiving space 27 of the dispensing device 1.

It is not mandatory for the test system to have a guide element that is structurally identical to the guide element 23 (which has or forms the receiving space 27) of the dispensing device 1, nor for the receiving space of the test system to be formed by a guide element 23 that is structurally identical to a guide element used in the dispensing device 1. Rather, what is critical for a simulation of the dispensing device 1 and/or the deformation of the sealing element 24 in the dispensing device 1 and/or the receiving space 27 is simply that the receiving space simulated in the test system corresponds as precisely as possible to the receiving space 27 of the dispensing device 1 in terms of dimensions and/or material. As mentioned, the test element of the test system is therefore preferably designed similarly or identically to the contact element 26. The test element is preferably made of the same material as the contact element 26, and/or the test element has the same diameter and/or cross section perpendicular to the axis A as the contact element 26.

Furthermore, it is preferred that the testing system has a plunger 29 and/or a central element 30. The conveying element 9 is preferably simulated by the plunger 29 and/or the central element 30. It is preferred that the plunger 29 and/or the central element 30 is made of the same material as the conveying element 9 and/or has the same diameter and/or cross section perpendicular to the axis A as the conveying element 9. The plunger 29 and the central element 30 will be described further below in more detail.

In the test system, components of the dispensing device 1 and/or of the pressure generator 5 that are not relevant to the sealing of the receiving space 27—for example, the discharge nozzle 12 or all parts that are not part of the pressure generator 5—are preferably omitted, and/or the test system does not have such components.

In this sense, the receiving space 27 and/or the pressure generator 5 and/or the dispensing device 1 is/are preferably merely simulated in the test system.

In the batch method and/or the batch-wise determination of the assembly parameter M, an assembly parameter M is preferably first determined for all sealing elements 24 of the random sample in the manner described below. The mean value is then preferably found from the assembly parameters M determined separately for the sealing elements 24 of the random sample. This mean value then preferably constitutes the assembly parameter M of the batch, and is used in particular for each installation of a sealing element 24 of the batch.

The assembly parameter M is preferably selected or set in such a way that for different batches of sealing elements 24 at least substantially the same ratio between the volume of the receiving space 27 and the volume of the sealing element 24 in the receiving space 27, and/or the same deformation value of the sealing element 24, results. In other words, the assembly parameter M is preferably selected such that the same deformation value or degree of filling of the sealing element 24 in the receiving space 27 results each time a dispensing device 1 is assembled. The seal and/or sealing effect is largely determined by the deformation value and/or degree of filling, such that a reliable seal can be achieved in this way even if there are differences between the sealing elements 24 of different batches.

An "equal" or "at least substantially the same" deformation value or degree of filling is preferably understood to mean degrees of filling or deformation values that differ only slightly from each other and/or are identical within a tolerance. In this respect, it is therefore possible that the same deformation values or degrees of filling do not match exactly, or deviate slightly from one another. Two deformation values or degrees of filling are in particular the same if they deviate by less than 10%, preferably less than 5%, in particular less than 2%, very particularly preferably less than 1%, from one another.

The assembly parameter M is preferably an adjustable, in particular geometric, value that must be observed when the dispensing device 1 is assembled, and/or which is implemented in the completely assembled dispensing device 1. The assembly parameter M can preferably be variably prespecified in the configurations of an assembly process. The assembly parameter M preferably represents a relative position of the fixing element 25 and/or contact element 26 in relation to the guide element 23, or corresponds thereto. The assembly parameter M is preferably a geometric parameter. In particular, the assembly parameter M or its value is an axial position of the fixing element 25 and/or contact element 26. In other words, this position is preferably defined by the assembly parameter M or its value. Since the position of the fixing element 25 and/or contact element 26, as explained above, preferably correlates with the volume of the receiving space 27, and thus preferably also with a deformation of the sealing element 24, the (batchwise) use or specification of the assembly parameter M makes it possible to ensure, in a simple manner, that reliable sealing of the conveying element 9 is achieved by the sealing element 24 with different batches of sealing elements 24.

It is also possible that the assembly parameter M corresponds only indirectly to a position of the fixing element 25 and/or contact element 26, for example by the assembly parameter M being defined or formed by a path distance that is traveled by part of an apparatus used for assembling the dispensing device 1 and/or for fastening the fixing element 25 to the guide element 23.

According to a further example in which the assembly parameter M corresponds in particular only indirectly to a position of the fixing element 25 and/or contact element 26, the assembly parameter M can be defined or formed by an angle of rotation, a screw travel position, or the like of a component to be fastened, in particular to be fastened by screw. In particular, the assembly parameter M can be formed by an angle of rotation, a screw travel position, or the like if the fixing element 25 is designed as a nut or cap nut, as explained above by way of example. By specifying an angle of rotation or screw travel position, the end position of the component or the nut, and thus indirectly its axial position and/or the height of the receiving space 27, can be defined.

Preferably, different assembly parameters M or different values of the assembly parameter M correspond to different volumes of the receiving space 27 and/or to different heights H of the receiving space 27. In other words, each assembly parameter M or each value of the assembly parameter M preferably corresponds to a specific volume of the receiving space 27 or a specific height H of the receiving space 27.

Alternatively or additionally, however, the assembly parameter M can also correspond to a specific force by means of which the sealing element 24 fixed in the receiving space 27 is deformed and/or fixed. The volume of the receiving space 27 or the height H of the receiving space 27 is in each case preferably directly correlated with a specific force or pressure with which the sealing element 24 is deformed in the receiving space 27. Therefore, instead of a geometric parameter such as a position of the contact element 26 or a height H of the receiving space 27, a specific force can also be used to define the assembly parameter M, or can be used as an assembly parameter M. In particular, this force then corresponds to a specific volume or a specific height H of the receiving space 27.

The volume or the height H of the receiving space 27 can preferably be set or fixed by means of the assembly parameter M. In particular, different assembly parameters M—more precisely, different values of the assembly parameter M—can be selected for different sealing elements 24 or different batches of sealing elements 24, such that the volume of the receiving space 27 can be adapted to each of the sealing elements 24 or the respective batch of sealing elements 24, and the same degree of filling or the same sealing effect or seal is achieved for different sealing elements 24 or batches of sealing elements 24.

Preferably, the assembly parameter M for a batch is initially determined using a subset or random sample of sealing elements 24 of the batch. Subsequently, the specific or selected assembly parameter M is preferably used each time a dispensing device 1 is assembled, or each time a sealing element 24 of the given batch is fixed in a receiving space 27. In particular, the assembly parameter M is a value that can be set (one time) during the assembly of the dispensing device 1, and/or does not have to be measured or determined, such that a plurality of dispensing devices 1 can be assembled quickly and efficiently, in particular in an automated manner.

The sealing elements 24 or dispensing devices 1 are preferably assembled in a process that is separate from the determination of the assembly parameter M and/or in a different system than the determination of the assembly parameter M.

The sealing elements 24 or dispensing devices 1 are preferably assembled in a fully automated process. In this case, in particular, a large number of dispensing devices 1 is assembled at high speed. In particular, several hundred or several thousand dispensing devices 1 are assembled per hour.

For assembly, a sealing element 24 is first placed in a receiving space 27 of a dispensing device 1. A fixing element 25 and/or contact element 26 is then inserted into the receiving space 27. As already described above, the fixing element 25 and the contact element 26 can either be formed by different components that are separate from each other, or constitute different portions of a single component. In a preferred embodiment, which is also shown in the figures, the fixing element 25 and the contact element 26 are formed by two separate components. In this case, the contact element 26 is inserted into the receiving space 27.

The fixing element 25 and/or contact element 26 is preferably moved far enough into the receiving space 27 that the sealing element 24 is deformed, and in particular the deformation value of the sealing element 24 reaches or exceeds the threshold value. In particular, the previously determined assembly parameter M is used for this purpose and preferably defines how far the fixing element 25 and/or contact element 26 is moved into the receiving element 27 or in which position the fixing element 25 and/or contact element 26, in particular the contact element 26, will be fixed by means of the fixing element 25.

The contact element 26 is preferably moved into the desired position by means of a stamp or plunger. The stamp or plunger can, for example, be designed in principle in a manner similar to the plunger 29—which is described in more detail later and is used to determine the assembly parameter M, and is shown in FIG. 4A—FIG. 4D. Preferably, however, the stamp or plunger used during assembly does not have a central element 30, and/or the stamp or plunger does not penetrate through the contact element 26 and/or the sealing element 24 during assembly.

The fixing element 25 is preferably pushed over the contact element 26 and/or the guide element 23 after the contact element 26 has been positioned in the position corresponding to the assembly parameter M or defined by the assembly parameter M.

However, it is also possible that the fixing element 25 is already pushed over the contact element 26 when the contact element 26 is positioned and/or is in contact with the contact element 26, such that the fixing element 25 and the contact element 26 are moved simultaneously in the direction of the sealing element 24. In this case, the contact element 26 is moved indirectly via the fixing element 25 in the direction of the sealing element 24. In this case, the stamp or plunger for moving the fixing element 25 and contact element 26 preferably contacts the fixing element 25 and acts only indirectly on the contact element 26 via the fixing element 25.

When the fixing element 25 and/or contact element 26 have reached the desired position and/or the position defined by the assembly parameter M or corresponding to the assembly parameter M, the fixing element 25 is preferably fastened or fixed to the guide element 23.

It is preferred that the fixing element 25 is additionally fixed or fastened to the contact element 26. "Fixing" a sealing element 24 is understood to mean, in particular, fixing or clamping the sealing element 24 in the receiving space 27 in such a way that the sealing element 24 cannot move in the receiving space 27 and/or cannot be undeformed—that is, in particular, cannot return to the undeformed original shape of the sealing element 24. This is preferably achieved in that the sealing element 24 is fixed or clamped in the receiving space 27 by means of the fixing element 25 and optionally by means of the contact element 26, with the fixing element 25 and/or contact element 26 pressing on the sealing element 24 and thus deforming it, such that the sealing element 24 bears against the boundaries of the receiving space 27 over a large area or as far as possible on all sides—that is, in particular, against the guide element 23 and/or the fixing element 25 and/or contact element 26. In the fully assembled dispensing device 1, the sealing element 24 also preferably rests against the conveying element 9 guided through the sealing element 24. The receiving space 27 and/or the guide element 23 and the fixing element 25 and/or contact element 26, and preferably the conveying element 9, preferably delimit or prevent further deformation of the sealing element 24 after assembly.

The sealing element 24 is therefore preferably fixed by the contact element 26 being fixed to, and/or by the fixing element 25 being fastened to, the guide element 23 and/or contact element 26. The height H and/or the volume of the receiving space 27 is preferably defined and/or fixed or determined by the fastening of the fixing element 25 to the guide element 23.

After the fixing element 25 and/or contact element 26 is/are fixed, the conveying element 9 is preferably installed. For this purpose, the conveying element 9 is inserted into the channel 23b through the fixing element 25, through the contact element 26 and/or sealing element 24. In principle, however, the conveying element 9 can also be installed or inserted before the fixing element 25 and/or contact element 26 is fixed.

During the assembly of the dispensing device, the relative position of the fixing element 25 and/or contact element 26 in relation to the guide element 23 can preferably be specified or adjusted by means of the assembly parameter M. Preferably, a distance measurement or height measurement takes place during assembly, by means of which measurement the height H of the receiving space 27 and/or the relative position of the fixing element 25 and/or contact element 26, in particular relative to the receiving space 27 or its base 27a and/or the guide part 23, is directly or indirectly verifiable and/or controllable. In this case, preferably all common path measuring methods can be used—for example, tactile, optical, or inductive methods, or the like.

In particular, by determining the assembly parameter M or its value in batches, it is not necessary to redetermine or readjust the assembly parameter M or its value each time a dispensing device 1 is assembled; rather, the assembly parameter M or its value is preferably initially (based on a subset or random sample of sealing elements 24 of the batch) determined for a batch and then used for each sealing element 24 of this batch. As a result, the method for assembling dispensing devices 1 can be simplified and accelerated.

The determination of the assembly parameter M will now be explained in more detail below, in particular with reference to FIGS. 4A to 4D and 5.

To determine the assembly parameter M, each of the sealing elements 24 is first arranged in the receiving space 27 or placed into the receiving space 27. The fixing element 25 and/or contact element 26 is then preferably placed on the sealing element 24 or brought into contact with the sealing element 24.

This is illustrated in FIG. 4A-FIG. 4D. FIG. 4A shows that the contact element 26 has already been inserted into the receiving space 27, but is not yet in contact with the sealing element 24. In FIG. 4B, the contact element 26 has been moved far enough into the receiving space 27 that it is in contact with the sealing element 24.

FIG. 4C shows the same situation as FIG. 4A. FIG. 4D shows the same situation as FIG. 4B. FIGS. 4C and 4D differ from FIGS. 4A and 4B only in that the sealing element 24 in FIGS. 4C and 4D has a smaller volume or a smaller diameter or a smaller thickness D than the sealing element 24 in FIGS. 4A and 4B.

The sealing element 24 is then preferably deformed in the receiving space 27 or pressed into the receiving space 27, in particular by means of the fixing element 25 and/or contact element 26. This is done in particular by exerting a force or pressure on the sealing element 24, in particular by means of the fixing element 25 and/or contact element 26. A deformation of the sealing element 24 by the contact element 26 for determining the assembly parameter M during the determination of the assembly parameter M is shown in particular in FIG. 4D.

The sealing element 24 is preferably deformed by a force acting axially on the sealing element 24, or by a pressure acting axially on the sealing element 24. In principle, however, it is also possible to alternatively or additionally deform the sealing element 24 by means of a radial force. A force acting radially inwards is preferably used in this case after the receiving space 27 has been delimited in the axial direction (that is, in particular after the fixing element 25 and/or contact element 26 has been placed thereon).

The force or pressure is preferably exerted on the sealing element 24, and/or the sealing element 24 is preferably deformed, by means of a plunger 29. In particular, the fixing element 25 and/or contact element 26 is moved in the direction of the sealing element 24 or into the receiving space 27 by means of the plunger 29, such that the fixing element 25 and/or contact element 26 contacts the sealing element 24, and deforms the sealing element 24 by exerting a force or pressure on it. The plunger 29 is shown by way of example in FIG. 4A-FIG. 4D.

The plunger 29 preferably acts only indirectly on the sealing element 24. It is preferably provided that the plunger 29 acts or presses, in particular axially, on the fixing element 25 and/or contact element 26. In particular, the plunger 29 is moved axially with respect to the fixing element 25 and/or contact element 26, such that the fixing element 25 and/or contact element 26 is thereby moved axially in the direction of the sealing element 24, and the sealing element 24 is thereby deformed.

The plunger 29 is preferably not a part of the dispensing device 1, but rather a part of a test system in which the assembly parameter M is determined.

For or during the determination of the assembly parameter M, a central element 30 is preferably guided into the channel 23b and/or through the (central) opening 24a of the sealing element 24. The volume of the receiving space 27 is preferably reduced or delimited by the central element 30. The central element 30 is shown by way of example in FIG. 4A—FIG. 4D.

In particular, the central element 30 constitutes an inner radial boundary of the receiving space 27 during the correlation measurement and/or determination of the assembly parameter M.

The central element 30 preferably has the same diameter or the same outer dimensions in the radial direction as the conveying element 9.

The central element 30 is preferably a portion of the plunger 29, or is formed as a single piece with the plunger 29. However, the central element 30 can also be formed separately from the plunger 29 and/or form a separate component.

The central element 30 can be tapered, conical, and/or rounded in at least one portion thereof, such that, when the central element 30 is pushed forward axially, the radial extension or width B of the receiving space 27 delimited by the central element 30 is reduced. In this way, the insertion of the central element 30 into the channel 23b or through the opening 24a of the sealing element 24 can be facilitated, and/or damage to the sealing element 24 can be prevented.

In principle, the central element 30 can also be formed by the conveying element 9.

During the correlation measurement or determination of the assembly parameter M, the sealing element 24 is preferably pressed against the central element 30 and, in particular, deformed in the process.

After the determination of the assembly parameter M, the central element 30 is preferably removed from the channel 23b or the opening 24a of the sealing element 24 again.

The assembly parameter M is preferably selected in such a way that, when the sealing element 24 is fixed, a deformation value corresponding to the deformation of the sealing element 24 reaches or exceeds a threshold value.

The deformation value "exceeding" the threshold value is understood to mean a situation in which the deformation value is initially less than the threshold value and then reaches a value that is greater than the threshold value, and vice versa—that is, when the deformation value is initially greater than the threshold value and then reaches a value that is less than the threshold value.

A plurality of threshold values can also be specified, with the assembly parameter M preferably being selected in such a way that the deformation value lies between the threshold values. In particular, the threshold values can therefore represent a maximum value and a minimum value for the deformation value.

The deformation value preferably corresponds to the deformation and/or a compression of the sealing element 24. In other words, the deformation value is preferably a value or a measure that indicates how much and/or in what way the sealing element 24 is deformed and/or compressed.

The deformation value is preferably determined indirectly using a characteristic value, as will be explained in more detail below.

Figure 5C:
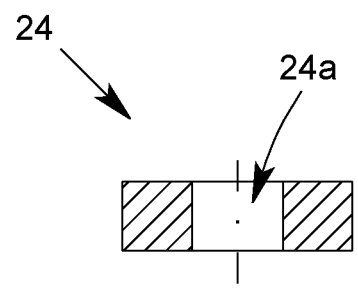
FIG. 5C is a schematic section of a deformed sealing element.

The deformation of the sealing element 24 is shown schematically in FIGS. 5B and 5C.

FIG. 5B shows the undeformed sealing element 24, in particular before it is placed in the receiving space 27. In the illustrated example according to FIG. 5B, the sealing element 24 has a circular cross section with a diameter or a thickness D. In principle, however, the sealing element 24 or its cross section can be of any shape.

A deformed sealing element 24 is shown in FIG. 5C. In particular, the illustration in FIG. 5C corresponds to a sealing element 24 inserted and fixed in a fully assembled dispensing device 1 and/or its receiving space 27. As can be seen from FIG. 5C, the sealing element 24 has been deformed in comparison to the initial situation in FIG. 5B, and is adapted in particular in its outer shape to the shape of the receiving space 27.

When the sealing element 24 is deformed, a preferably elastic deformation occurs first, in which the volume of the sealing element 24 does not (significantly) change, or only the outer shape of the sealing element 24 is changed or adapted to the receiving space 27. Typically, with a further increase in the exertion of pressure and/or force and/or deformation of the sealing element 24 following the simple change in shape, a volume compression—that is, change or reduction in volume—of the sealing element 24 begins, in particular in addition to the primarily pure change in shape.

The threshold value particularly preferably corresponds to a deformation value which corresponds to this onset of the volume compression of the sealing element 24, or at which the volume compression begins or starts. Depending on the material of the sealing element 24, however, it can also be desirable or advantageous to choose a value as the threshold value that is specifically above or below the value at which the volume compression starts. For example, for a material with high creep behavior, for example a thermoplastic elastomer (TPE), it can be advantageous to set the threshold value in such a way that volume compression has not yet started.

The assembly parameter M is preferably determined based on the deformation behavior and/or friction behavior of the sealing element 24 during a deformation of the sealing element 24 in the receiving space 27.

The examination or determination of the deformation behavior and/or friction behavior is explained in more detail below with reference to FIG. 4A—FIG. 4D and FIG. 5.

To examine or determine the deformation behavior, an (increasing) force is preferably exerted on the sealing element 24 by means of the plunger 29, fixing element 25, and/or contact element 26, and the sealing element 24 is thereby deformed. In particular, for a plurality of different deformations or deformation values of the sealing element 24, the force required to achieve this deformation or this deformation value is determined in each case. A displacement corresponding to the force is preferably also determined.

To examine or determine the friction behavior, a boundary of the receiving space 27, in particular the central element 30, and the sealing element 24 are preferably moved relative to one another, and the frictional force between the sealing element 24 and the boundary is determined in each case at several points in time during the deformation.

The deformation value is preferably determined at least indirectly by or during the examination or determination of the deformation behavior and/or friction behavior of the sealing element 24. However, the deformation value itself does not have to be determined or known directly. For example, it is possible that a specific deformation value corresponding to the forces and/or frictional forces between the sealing element 24 and the boundary that are required for the deformation is known from previous tests.

A characteristic value is preferably measured to examine the deformation and/or friction behavior. In particular, conclusions can be drawn about the deformation value, or the deformation value can be determined, via the characteristic value. In other words, the characteristic value is preferably a variable or a value that is determined or measured in order to determine, calculate and/or derive the deformation value from the characteristic value. The characteristic value is preferably correlated with the deformation value. Therefore, a specific deformation value preferably corresponds to each value of the characteristic value.

The characteristic value is preferably a force and/or a pressure which is/are exerted on the sealing element 24 for the purpose of deformation, and/or a position, in particular an axial position, of the plunger 29 with which the sealing element 24 is deformed. In other words, the force and/or the pressure with which the sealing element 24 is deformed is preferably measured, and/or the position of the plunger 29 at which the sealing element 24 is deformed is measured. In particular, the force can be known indirectly from the position of the plunger 29. As a result, the desired deformation value, or—as a result thereof—a reliable seal and/or sealing effect can be achieved for different sealing elements 24.

In each case, the force is preferably related to a specific area, in particular the area of the receiving space 27 and/or the base 27a. In this respect, the force in each case corresponds directly to a pressure, or the force is in each case a force normalized or related to an area. The term "force" is preferably also interchangeable with the term "pressure."

The deformation behavior is preferably determined by means of the force or the pressure that is exerted on the sealing element 24 for the deformation. Alternatively or additionally, the deformation behavior is determined (indirectly) by means of a position, in particular an axial position, of the plunger 29 and/or the fixing and/or contact element 25, 26. The position of the plunger 29 and/or the fixing and/or contact element 25, 26, in particular, a height H of the receiving space 27.

In particular, the height H of the receiving space 27 or a variable correlated thereto, such as a travel path or axial position of the plunger 29 and/or fixing and/or contact element 25, 26, can be specified or set, and the force corresponding thereto can be determined or measured. In a reversal of this principle, however, it is also possible to specify or set the force and to determine or measure the height H of the receiving space 27 corresponding to the particular force that is set or specified in each case, or corresponding to the variable correlated thereto.

The force and/or the pressure and/or the position of the plunger 29 is/are preferably measured. However, it is also possible for the force, the pressure, and/or the position to be known, prespecified, or calculable or determinable without an explicit measurement, for example from the magnitude of a control parameter used to move the plunger 29, such as an (electrical) voltage or the like by which the force exerted by the plunger 29 is controlled or regulated.

Alternatively or additionally to determining the deformation behavior of the sealing element 24 during a deformation, as already mentioned, the friction behavior can also be determined while the sealing element 24 is being deformed. The deformation of the sealing element 24 in the receiving space 27 can also be measured (indirectly) by measuring an auxiliary measurement variable, such as a frictional force, which occurs between the sealing element 24 and a boundary of the receiving space 27 which is in contact with the sealing element 24 and which is moved relative to the sealing element 24. The frictional force increases as the contact pressure of the sealing element 24 on the boundary increases, with the increase in the frictional force depending on the deformation that occurs in the sealing element 24 and/or on the size of the contact surface between the sealing element 24 and the boundary of the receiving space 27. In particular, the contact pressure increases with increasing deformation of the sealing element 24, which results in a changed, in particular increased, frictional force between the sealing element 24 and the boundary of the receiving space 27. Initially, an at least predominantly elastic deformation of the sealing element 24 takes place. This gradually turns into a compression of the sealing element 24 upon increasing deformation. In particular, the increase and/or slope of the frictional force is greater when the sealing element 24 is compressed than when the sealing element is elastically deformed. It is thus possible to draw conclusions about the deformation or the deformation behavior of the sealing element 24 via the friction behavior—in particular, to (indirectly) determine the deformation or the deformation behavior of the sealing element 24.

In order to determine the friction behavior, the sealing element 24 is preferably moved relative to a boundary of the receiving space 27. This can be done, for example, by moving the plunger 29 or the central element 30 relative to the sealing element 24, in particular axially or along the axis A. In this case the central element 30 forms the boundary of the receiving space 27, which boundary is moved relative to the sealing element 24. In this case, the plunger 29 or the central element 30 is preferably oscillated or moved back and forth. In particular, the force required to move the plunger 29 or central element 30 is measured. This measured force preferably corresponds to the frictional force between the plunger 29 or central element 30 and the sealing element 24 or is correlated therewith. The characteristic value, as a (particularly indirect) auxiliary measured value, preferably represents the measured force and/or friction force. From it, the deformation value, and therefore in particular also the threshold value, is determined, calculated, or derived.

In this method, it is preferably provided that the fixing element 25 and/or contact element 26 is fixed or moved or pressed into the receiving space 27 by means of a further plunger (not shown in FIG. 4A-FIG. 4D).

In principle, however, the frictional force can also be measured in another way, for example by rotating the plunger 29 or the central element 30 relative to the sealing element 24 and/or about the axis A and measuring the torsional friction or torsional frictional force that occurs.

An advantage of determining the frictional behavior during the deformation of the sealing element 24 is that the long-term behavior of the sealing element 24 in the dispensing device 1 can be predicted by a short-term test—namely, the measurement of the frictional force.

A further advantage of determining the frictional behavior during the deformation of the sealing element 24 is that the threshold value and/or assembly parameter M is determined directly using a parameter or characteristic value, namely the frictional force, which has effects on the properties of the aerosol 14 generated with the dispensing device 1. The greater the frictional force between the sealing element 24 and the conveying element 9, which frictional force occurs when the conveying element 9 is moved to generate the aerosol 14, the less energy is available for generating the aerosol 14 from the fluid, since part of the total energy available is lost through friction. Excessive frictional force therefore means that the droplets of the aerosol 14 produced have a more uneven and/or smaller size, and/or the duration of a spray burst is impacted—in particular, shortened. This has a negative impact on the effectiveness and precise dosing of the drug sprayed with the dispensing device 1 as an aerosol 14.

In particular, a force/displacement curve is recorded to examine or determine the deformation behavior or friction behavior and/or to determine the assembly parameter M. The assembly parameter M is very particularly preferably determined using the profile of the force/displacement curve.

In FIG. 5A, a force/displacement curve is shown by way of example. Here, a displacement is plotted on the x-axis, and a force F is plotted on the y-axis.

The displacement is represented by the height H of the receiving space 27 in FIG. 5A. However, the displacement can also correspond to the distance traveled or to the position of the plunger 29 and/or fixing and/or contact element 25, 26 with which the sealing element 24 is deformed. The displacement can be measured or known in some other way, for example from a control parameter such as an electrical voltage or the like by means of which the travel distance of the plunger 29 and/or fixing and/or contact element 25, 26 is controlled or regulated. In particular, a specific value of the displacement or the height H corresponds to a specific volume of the receiving space 27.

The force F is, for example, the already explained force that is exerted on the sealing element 24 for the purpose of deformation or a variable corresponding thereto, such as the exerted pressure and/or the frictional force occurring during the relative movement between the sealing element 24 and the boundary of the receiving space 27 or the central element 30.

A specific deformation or a specific deformation value of the sealing element 24 preferably corresponds to a specific force that is required to achieve this deformation or this deformation value and/or to a specific height H of the receiving space 27, or a variable correlated thereto, at which this deformation or this deformation value is reached. In particular, the deformation value can therefore be determined by means of the force and/or the height H.

Two different forces F1, F2 and the associated displacements and/or heights H1, H2 are shown in FIG. 5A by way of example. The displacement or the height H is preferably correlated with the distance traveled and/or the position of the plunger 29 with which the sealing element 24 is deformed.

FIG. 5A is explained below "from right to left"—that is, starting with large values of H. The force/displacement curve starts at the value D for the height H, where D is the height of the undeformed sealing elements 24, in particular the axial height and/or cross section height of a ring-shaped sealing element 24—particularly preferably the thickness of a toroidal sealing element 24, as shown for example in FIG. 5B. At this point, the fixing element 25 and/or contact element 26 contacts the still undeformed sealing element 24, as shown for example in FIG. 4B. At this point, the force F has the value zero, since no deformation has yet taken place and/or no force is being exerted on the sealing element 24.

For the deformation or (elastic) deformation of the sealing element 24, preferably only a small amount of force is initially required. With increasing deformation, the force initially increases slightly, as shown in FIG. 5A. This can be seen from the only-slight increase in force F from point H=D to point H=H1. Lower values of H in this case correspond to greater deformation of the sealing element 24, since with lower values of H, and correspondingly an axial travel path of the plunger 29 in the direction of the sealing element 24 and/or receiving space 27, the volume of the receiving space 27 is reduced and the sealing element 24 accordingly is pressed further or more firmly into the receiving space 27 and is thereby deformed.

Due to the elasticity of the sealing element 24, the force required purely for the change in shape or deformation is relatively small.

As the height H decreases, the volume of the receiving space 27 decreases, and thus the degree of filling—that is, the ratio of the volume of the sealing element 24 to the receiving space 27—decreases.

The force F increases with decreasing height H and/or decreasing volume of the receiving space 27.

In particular, as the height H continues to decrease, compression of the sealing element 24 begins, as already explained. When the compression begins, the slope of the force/displacement curve increases in particular, since a greater force is required to compress the sealing element 24 than for a pure change in shape.

The deformation, in particular the onset of compression, can therefore be read or determined in particular from the force/displacement curve and/or its profile, in particular its slope and/or curvature.

In particular, the slope and/or curvature of the force/displacement curve changes when the volume compression of the sealing element 24 begins. In the example shown in FIG. 5A, this takes place in particular approximately between the positions H1 and H2 and/or the values F1 and F2 shown in the drawing. If the height H is reduced even further, a volume compression substantially or predominantly takes place. A high force is required for this, such that high forces F are reached in the left-hand region in FIG. 5A, and the force/displacement curve has a high slope or rises steeply (towards smaller values of H).

The onset of volume compression preferably corresponds to the strongest curvature of the force/displacement curve. When the volume compression begins, the force/displacement curve may also have an inflection point or the like. In particular, the onset of volume compression can therefore be determined reliably and precisely by a derivation of the force/displacement curve, for example by the derivation of the force/displacement curve having a discontinuity or other sharp change in the profile when volume compression begins.

In order to determine the assembly parameter M, the force/displacement curve is preferably used to determine or ascertain when volume compression of the sealing element 24 begins, and/or a specific characteristic value K is determined at which the volume compression of the sealing element 24 begins and/or which corresponds to an onset of the volume compression.

In other words, the specific characteristic value K is in particular the value of the characteristic value at which the volume compression of the sealing element 24 begins.

According to the above explanations, the volume compression begins in particular at the point at which the force/displacement curve has the strongest curvature and/or an inflection point. The specific characteristic value K therefore preferably corresponds to the force at which the force/displacement curve has the (at least substantially) greatest curvature and/or an inflection point, and correlates in the illustrated example according to FIG. 5A with a height HM desired or preferred in the assembly, which in turn correlates with the desired assembly parameter M.

Different profiles of the force/displacement curve and thus different specific characteristic values K and/or heights HM and/or assembly parameters M can result for different sealing elements 24 or batches of sealing elements 24.

The assembly parameter M is preferably selected or determined in such a way that it corresponds to an onset of volume compression of the sealing element 24. In accordance with the above explanations, the assembly parameter M is therefore preferably selected such that the height of the receiving space 27 in the completely assembled dispensing device 1 corresponds at least substantially to the height HM at which the force/displacement curve has the greatest curvature and/or an inflection point. In particular, the assembly parameter M corresponds to the height HM of the receiving space 27 at which the volume of the (deformed) sealing element 24 corresponds to the volume of the receiving space 27, or a degree of filling of at least substantially 100% is reached.

However, the assembly parameter M can also be selected or determined in such a way that it corresponds to a different deformation or a different deformation value of the sealing element 24, for example to a deformation value at which the volume compression has not yet started or at which the sealing element 24 is still not compressed, and/or in which the sealing element 24 is only, or at least predominantly, elastically deformed. Preferably, a defined difference can be selected between the deformation value that corresponds to the assembly parameter M and the deformation value that corresponds to an onset of volume compression. It is also possible to select or determine the assembly parameter M in such a way that it corresponds to a deformation or a deformation value of the sealing element 24 at which the volume compression has already started, and/or the sealing element 24 is already compressed.

The assembly parameter M can therefore also correspond to other degrees of filling or correspond to a degree of filling other than 100%, for example an (arbitrary) degree of filling of more than 95% and/or less than 105%. Depending on the material of the sealing element 24, this can be advantageous or lead to a better seal and/or service life than a degree of filling of 100%.

The conditions under which, and/or at which specific characteristic value, in particular at which force in the force/displacement curve, the deformation value reaches or exceeds a desired threshold value, are preferably determined for each batch using a random sample. Then the assembly parameter M is selected such that the deformation value reaches or exceeds the threshold value when a sealing element 24 of the batch is installed. The assembly parameter M therefore corresponds in particular to the corresponding height HM and/or the specific characteristic value K. The selection of the assembly parameter M is preferably carried out in that the same volume of the receiving space 27 is implemented at or through the position in which the fixing element 25 is fastened to the guide element 23, and/or the contact element 26 is fixed in a position, as is the case when the deformation value corresponds to the threshold value when the assembly parameter M is determined by means of the deformation of the plunger 29, and/or the deformation value assumes the threshold value. In other words, the assembly parameter M is preferably chosen so that the height (and thus in particular the volume) of the receiving space 27 of the fully assembled dispensing device 1 has the same value as the travel path or the height HM in the force/displacement curve which corresponds to the specific characteristic value K.

For the determination and/or during the determination of the assembly parameter M, the deformation value to which the selected or determined assembly parameter M corresponds is preferably exceeded. For example, the value F2 shown in FIG. 5A can be the maximum force that is exerted on the sealing element 24 when the assembly parameter M is determined; and the assembly parameter M shown in FIG. 5A can be the selected or determined assembly parameter M. The determination of the assembly parameter M therefore preferably proceeds along the force/displacement curve beyond a height H to which the assembly parameter M corresponds. This is due in particular to the fact that the highest curvature or slope can only be reliably determined when the point of the strongest curvature or slope has already been exceeded.

In the batch method explained so far, as described above, the assembly parameter M for a batch of sealing elements 24 is first determined in a separate process, in particular using a random sample, and then used during the assembly of the sealing elements 24 of the batch.

However, the separation of the steps of determining the assembly parameter M and the actual assembly of a dispensing device 1 is not mandatory.

According to a further aspect that can also be implemented independently, which is described below, the present invention also relates to a method for assembling dispensing devices 1, in which an assembly parameter M is first determined for a sealing element 24, and the sealing element 24 is fixed in the receiving space 27 immediately after the determination of the assembly parameter M, and/or the assembly of the dispensing device 1 takes place immediately after the determination of the assembly parameter M. In this case, in contrast to the batch method described above, the sealing element 24 is preferably fixed in the dispensing device 1 or the receiving space 27 in which the assembly parameter M is also determined. In particular, the determination of the assembly parameter M and the assembly of the dispensing device 1 take place immediately after one another and/or in the same system. This method is referred to in particular as the individual method.

The individual method is advantageous in particular when an assembly, in particular an automatic or series assembly, of dispensing devices 1 will be performed without a prior determination of an assembly parameter M. This can be the case in particular when the sealing elements 24 of a batch, or their significant dimensions, deviate too greatly from one another. In this case, it may not be possible to determine a common assembly parameter M for all sealing elements 24 of the batch, and/or a reliable seal and/or sealing effect cannot be ensured by determining a single assembly parameter M for all sealing elements 24 of the batch.

Nevertheless, the individual method described in more detail below can in principle also be used if the sealing elements 24 are present in batches and the sealing elements 24 of a batch deviate so little from one another that the batch method could also be used in principle.

In the individual method, the assembly parameter M is preferably determined—at least substantially—as described above for the batch method in connection with FIG. 4A—FIG. 4E and FIG. 5, in particular on the basis of the determination of the deformation behavior and/or friction behavior of the sealing element 24 during a deformation in the receiving space 27, and/or based on the profile of a force/displacement curve.

The above statements regarding the determination of the assembly parameter M therefore preferably also apply to the individual method.

In contrast to the plunger 29 shown in FIG. 4A—FIG. 4D, which is used in the batch method, in the individual method the plunger 29 preferably has no central element 30 and/or the plunger 29 does not pass through the contact element 26 and/or the sealing element 24.

Preferably, however, instead of the central element 30, the conveying element 9 is already guided through the contact element 26 and/or the sealing element 24 and/or is inserted into the channel 23b during the determination of the assembly parameter M. In this sense, the central element 30 is preferably replaced by the conveying element 9. The above statements with regard to the central element 30 therefore preferably apply analogously to the method in which the conveying element 9 is used instead of the central element 30.

As described for the batch method, the sealing element 24 is also deformed in the individual method for determining the assembly parameter M, with the desired deformation of the sealing element 24 or the desired deformation value of the sealing element 24 being exceeded when the assembly parameter M is determined.

Accordingly, after the determination of the assembly parameter M has taken place or has been completed, the plunger and thus the fixing element 25 and/or contact element 26 are preferably moved back a little—that is, in particular in the direction of the fixing element 25 and/or contact element 26 facing away from the sealing element 24. In particular, the fixing element 25 and/or contact element 26 is thereby positioned such that the assembly parameter M is implemented and/or the position of the fixing element 25 and/or contact element 26 corresponds to the specific assembly parameter M. The result of this is that the sealing element 24 assumes the desired deformation value, and/or the desired deformation value is implemented.

The fixing element 25 and/or contact element 26 or sealing element 24 is then preferably fixed in this position, in particular by fixing or fastening the fixing element 25 to the guide element 23 or guide portion 23a and/or the contact element 26. The fixing element 25 is preferably fastened as described above, for example by crimping.

In particular, in the case of the individual method, the fixing or the assembly of the sealing element 24 or the dispensing device 1 takes place immediately after the determination of the assembly parameter M and/or in the same system as the determination of the assembly parameter M.

In contrast to the batch method, the fixing element 25 is preferably entrained during the determination of the assembly parameter M in the individual method. In the embodiment of the fixing element 25 and contact element 26 as separate parts, as shown in the figures, in the batch method, as explained above, preferably only the contact element 26 is inserted into the receiving space 27, and/or the sealing element 24 is only deformed with the contact element 26. In the case of the individual method, on the other hand, the fixing element 25 is preferably entrained when the assembly parameter M and/or deformation of the sealing element 24 is determined by means of the contact element 26, such that, immediately after the assembly parameter M has been determined and/or the contact element 26 and/or fixing element 25 has been correctly positioned, the fixing element 25 can be fixed in this position or fastened to the guide element 23.

A "medicament" within the meaning of the present invention is a substance or a preparation of substances that is intended for use in or on a human or animal body, and is intended as an agent with properties for healing or alleviating or preventing human or animal diseases or pathological conditions, or which can be applied to or administered to a human or animal body or administered to a human or animal either to restore, correct, or affect physiological functions through a pharmacological, immunological, or metabolic effect, or to make a medical diagnosis.

An "assembly parameter" within the meaning of the present invention is preferably an adjustable and/or geometric value that is prespecified and/or that must be observed during assembly of the dispensing device or can be implemented or is implemented in the completely assembled dispensing device. The assembly parameter can preferably be prespecified in a variable manner in the configurations of an assembly process. The assembly parameter is preferably a geometric parameter, in particular a, preferably relative, position of a component, or a linear dimension such as a height of the receiving space of the dispensing device. In particular, the assembly parameter is a position of a fixing element relative to a guide element, the sealing element being fixed in the guide element and/or in a receiving space of the guide element by means of the fixing element. In other words, this position is preferably defined by the assembly parameter or its value. It is also possible that the assembly parameter only indirectly corresponds to a position of the fixing element and/or contact element, for example by the assembly parameter being defined or formed by a displacement path that is traveled, or the like, by a part of an apparatus for assembling the dispensing device and/or for fastening the fixing element to the guide element.

A "deformation value" within the meaning of the present invention is preferably a measure of how severely the sealing element is deformed, and in particular compressed. In particular, the deformation value is a value that corresponds to a deformation of the sealing element or indicates a deformation of the sealing element. The deformation value can, for example, be determined, calculated, and/or derived from one or more measured values or characteristic values. The deformation value preferably indicates whether and/or to what extent the sealing element is (elastically) deformed and/or compressed. In particular, the deformation value is a (temporary) property or a temporary state of the sealing element which cannot be measured or determined directly, but which is preferably determined, calculated or derived from a measured characteristic value.

A "threshold value" within the meaning of the present invention is preferably a value or limit value that is used to select or determine the assembly parameter. The threshold value is in particular a specific value or limit value of the deformation value. The assembly parameter is preferably selected or determined in such a way that when the sealing element is fixed, the deformation value reaches or exceeds the threshold value. The threshold value is preferably prespecified or can be prespecified. The threshold value preferably corresponds to an onset of volume compression of the sealing element, and/or the threshold value is that value of the deformation value at which volume compression of the sealing element begins. Depending on the material of the sealing element, however, it can also be desirable or advantageous to choose a value as the threshold value that is specifically above or below the value at which the volume compression begins.

A "characteristic value" within the meaning of the present invention is preferably a value that is determined or measured in order to determine the deformation value, to calculate it, and/or to derive it from the characteristic value. The characteristic value can be a, in particular measured, force (in particular, a pressure or a friction force), a pressure, or a position, for example. In particular, the characteristic value is therefore a measured value from which it is possible to draw conclusions about the deformation value.

A "compression set" within the meaning of the present invention is preferably a material property of a material from which a sealing element is made. In particular, the compression set is a measure of how the material, in particular an elastomer, behaves in the event of long-lasting and/or constant compression deformation and preferably subsequent relaxation. The compression set is preferably determined according to DIN ISO 815-1:2016-09. To determine the compression set, a cylindrical test specimen is preferably compressed, in particular by 25%, and stored at a specific temperature for a specific period of time. After unloading, preferably 30 minutes after unloading, the permanent deformation of the test specimen is determined from the comparison between the height of the test specimen before compression and the height of the test specimen after unloading. In particular, a compression set of 0% means that the test specimen has fully regained its original height. A compression set of 100% means that the body was fully deformed during the test and shows no recovery. In particular, the compression set is the ratio (L0–L2)/(L0–L1), where L0 is the height of the test specimen before the test, L1 is the height of the test specimen during the test, and L2 is the height of the test specimen after the test.

A "creep behavior" or "creep" of a material or sealing element within the meaning of the present invention is in particular the behavior of the material or sealing element under constant load. In particular, the creep behavior or creep is a time- and/or temperature-dependent plastic deformation under a constant load. The creep behavior or creep is determined or characterized in particular by the creep modulus.

A "fixing" of a sealing element in a receiving space within the meaning of the present invention is in particular a fixing or fixation of the sealing element in the receiving space in such a way that the sealing element in the receiving space is not or cannot be deformed any further.

The aspects and features explained above can be implemented independently of one another, but also in various combinations. In particular, the batch method and the individual method can be combined with one another. In other words, steps that have been explained in connection with the batch method can also constitute steps of the individual method, and vice versa.

LIST OF REFERENCE SIGNS 1 dispensing device
2 medicament
3 container
4 fluid space
5 pressure generator
6 holder
7 drive spring
8 locking element
8a trigger button
9 conveying element
10 check valve
11 pressure chamber
12 discharge nozzle
13 mouthpiece
14 aerosol
15 supply air opening
16 (upper) housing part
17 inner part
17a upper part (inner part)
17b lower part (inner part)
18 (lower) housing part
19 retaining element
20 spring
21 container base
22 piercing element
23 guide element
23a fastening portion
23b channel
23c recess
24 sealing element
24a opening
25 fixing element
25a counter surface
26 contact element
26a contact portion 26a
26b stop
26c insertion portion
27 receiving space
27a base
28 supply channel
29 plunger
30 central element
31 positioning device
31a helix structure
31b locking elements
A axis
B width
D thickness
F force K specific characteristic value
H height
HM height for assembly
M assembly parameter

The invention claimed is:

1. A method for assembling dispensing devices (1) for dispensing a medicament (2), where each of the dispensing devices (1) includes: (i) a conveying element (9) which is axially movable for conveying the medicament (2), (ii) a guide element (23) for guiding the conveying element (9), and a ring-shaped sealing element (24) for sealing the conveying element (9) against the guide element (23), and where the guide element (23) at least partially delimits a receiving space (27) for fixedly receiving the ring-shaped sealing element (24), the method comprising:
   arranging the ring-shaped sealing element (24) in the receiving space (27) of a given one of the dispensing devices (1), or in a test receiving space of a test system, wherein the test receiving space has a same dimensioning as the receiving space (27) of the given one of the dispensing devices (1),
   deforming the ring-shaped sealing element (24) while in the test receiving space and determining deformation behavior and/or friction behavior of the ring-shaped sealing element, and
   determining an assembly parameter (M) on a basis of the deformation behavior and/or friction behavior of the sealing element (24) determined during the deforming of the ring-shaped sealing element, where the assembly parameter (M) is at least one or more fixed or adjustable dimensions and/or relative positions among one or more components of respective ones of the dispensing devices (1) which will correspond to a deformation value of the sealing element (24) that reaches or exceeds a threshold value when the sealing element is fixed in a dispensing device,
   wherein at least one of: (i) the sealing element (24), or a different sealing element (24) is installed in the receiving space (27) of the dispensing device (1) using the assembly parameter (M) to obtain said deformation value, (ii) a further sealing element (24) is installed in the receiving space (27) of a further one of the dispensing devices (1) using the assembly parameter (M) to obtain said deformation value.

2. The method according to claim 1, wherein the sealing element (24) is one of a plurality of sealing elements (24) provided in batches, and the assembly parameter is among a plurality of respective assembly parameters (M) determined separately for each of the batches using a random sample of the sealing elements (24) from each of the batches, wherein a given one of the assembly parameters (M) determined for a given one of the batches is used for each fixing of each sealing element (24) of the plurality of sealing elements (24) of the given one of the batches in the receiving space (27).

3. The method according to claim 2, wherein each of the assembly parameters (M) is selected in such a way that a deformation value results for completely assembled dispensing devices (1) that is the same for different batches of the sealing elements (24), wherein the deformation value is a measure of how much the sealing element (24) is at least one of: (i) deformed, and (ii) compressed.

4. The method according to claim 2, wherein to determine the assembly parameter (M) of a batch, an assembly parameter (M) is first determined separately for each sealing element (24) in the random sample, and a mean value of these assembly parameters (M) determined separately is defined as the assembly parameter (M) for all sealing elements (24) of the batch.

5. The method according to claim 2 wherein to determine the assembly parameter (M), a central element (30) is guided through an opening (24a) in the sealing element (24) and/or through the receiving space (27), and a volume of the receiving space (27) is reduced or delimited by the central element (30).

6. The method according to claim 2, wherein at least one of:
- a number of sealing elements (24) in the random sample is one of: less than 50%, less than 20%, less than 10%, less than 5%, and less than 2%, of the number of sealing elements (24) of the batch, and
- the volumes of the sealing elements (24) of a batch deviate by one of: less than 10%, less than 5%, and less than 4%, from a mean volume of the sealing elements (24) of the batch.

7. The method according to claim 1, wherein the sealing element (24) is permanently fixed in the receiving space (27) immediately after the deformation and determination of the assembly parameter (M) by means of a fixing element (25) or contact element (26) acting on the sealing element (24).

8. The method according to claim 1, wherein the assembly parameter (M) is determined separately for each sealing element (24) to be installed and is used in each case only when fixing the sealing element (24) for which it was determined.

9. The method according to claim 1, wherein at least one of:
- the assembly parameter (M) is at least one of an adjustable and/or geometric value which is prespecified for or implemented in assembly of the dispensing device (1), and
- the assembly parameter (M) is prespecified in a variable manner in configurations of an assembly process.

10. The method according to claim 1, wherein at least one of:
- the assembly parameter (M) is at least one of a position, and an axial position, of a fixing element (25) or contact element (26) relative to one of the receiving space (27) and a guide element (23) of the dispensing device (1), and
- the position is defined by the assembly parameter (M) where the guide element (23) at least partially delimits the receiving space (27), and the fixing element (25) or contact element (26) is used for fixing the sealing element (24) in the receiving space (27).

11. The method according to claim 1, wherein the assembly parameter (M) corresponds to at least one of a volume of the receiving space (27), a deformation value, and an onset of volume compression, of the sealing element (24).

12. The method according to claim 1, wherein at least one of:
- the deformation value is a measure of how much the sealing element (24) is deformed, and
- the threshold value corresponds to an onset of volume compression of the sealing element (24).

13. The method according to claim 1, wherein to determine the deformation behavior and/or friction behavior of a plurality of sealing elements (24) with different deformations, in each case a characteristic value is measured which corresponds to a deformation value of the sealing element (24) and/or from which the deformation value of the sealing element (24) can be calculated, determined, and/or derived.

14. The method according to claim 13, wherein the characteristic value is at least one of a force, a frictional force, a compressive force, a pressure, and a position.

15. The method according to claim 1, wherein to determine the deformation behavior of a plurality of sealing elements (24), a force required for deformation is determined for each of different deformations.

16. The method according to claim 1, wherein to determine the friction behavior of a plurality of sealing elements (24), the sealing element (24) and a boundary of the receiving space (27) are moved relative to one another, and a frictional force between the sealing element (24) and the boundary is determined for each of different deformations.

17. The method according to claim 1, wherein at least one of:
- a force/displacement curve is recorded to determine the deformation behavior or friction behavior and/or to determine the assembly parameter (M), and
- the assembly parameter (M) is determined on the basis of a profile and/or the curvature of the force/displacement curve.

18. The method according to claim 1, wherein the sealing element (24) is designed to seal the conveying element (9) for conveying the medicament (2) against the guide element (23) which comprises or forms the receiving space (27) and in which the conveying element (9) is guided.

19. A dispensing device (1) for dispensing the medicament produced by the method of claim 1.

* * * * *